United States Patent
Hoey et al.

(10) Patent No.: US 9,924,992 B2
(45) Date of Patent: Mar. 27, 2018

(54) MEDICAL SYSTEM AND METHOD OF USE

(75) Inventors: Michael Hoey, Shoreview, MN (US); John H. Shadduck, Menlo Park, CA (US)

(73) Assignee: Tsunami MedTech, LLC, Menlo Park, CA (US)

( * ) Notice: Subject to any disclaimer, the term of this patent is extended or adjusted under 35 U.S.C. 154(b) by 508 days.

(21) Appl. No.: 12/389,808

(22) Filed: Feb. 20, 2009

(65) Prior Publication Data

US 2009/0216220 A1    Aug. 27, 2009

Related U.S. Application Data

(60) Provisional application No. 61/126,647, filed on May 6, 2008, provisional application No. 61/126,651, filed on May 6, 2008, provisional application No. 61/126,612, filed on May 6, 2008, provisional application No. 61/126,636, filed on May 6, 2008, provisional application No. 61/130,345, filed on May 31, 2008, provisional application No. 61/191,459, filed on Sep. 9, 2008, provisional application No. 61/066,396, filed on Feb. 20, 2008, provisional (Continued)

(51) Int. Cl.
 *A61B 18/08* (2006.01)
 *A61B 18/10* (2006.01)
 *A61B 18/00* (2006.01)

(52) U.S. Cl.
 CPC ........... *A61B 18/082* (2013.01); *A61B 18/10* (2013.01); *A61B 2018/00029* (2013.01); *A61B 2018/00642* (2013.01); *A61B 2018/00791* (2013.01); *A61B 2218/005* (2013.01)

(58) Field of Classification Search
 CPC ....... A61B 18/08; A61B 18/082; A61B 18/10; A61B 2018/00029; A61B 2018/00642; A61B 2018/00791; A61B 2218/005
 USPC ............ 606/27, 41, 42, 45–50; 607/101–102
 See application file for complete search history.

(56) References Cited

U.S. PATENT DOCUMENTS

| 408,899 A | 8/1889 | Bioch et al. |
| 697,181 A | 4/1902 | Smith |

(Continued)

FOREIGN PATENT DOCUMENTS

| WO | WO 2000/011927 | 3/2000 |
| WO | WO 2000/029055 | 5/2000 |

(Continued)

OTHER PUBLICATIONS

Moulding et al., "Preliminary studies for achieving transcervical oviduct occlusion by hot water or low-pressure steam," *Advancesin Planned Parenthood*, vol. 12, No. 2: pp. 79-85, 1977.

(Continued)

*Primary Examiner* — Ronald Hupczey, Jr.
*Assistant Examiner* — Khadijeh Vahdat
(74) *Attorney, Agent, or Firm* — Levine Bagade Han LLP

(57) ABSTRACT

An instrument and method for tissue thermotherapy including an inductive heating means to generate a vapor phase media that is used for interstitial, intraluminal, intracavity or topical tissue treatment. In one method, the vapor phase media is propagated from a probe outlet to provide a controlled vapor-to-liquid phase change in an interface with tissue to thereby apply ablative thermal energy delivery.

25 Claims, 21 Drawing Sheets

Related U.S. Application Data application No. 61/123,416, filed on Apr. 8, 2008, provisional application No. 61/068,049, filed on Mar. 4, 2008, provisional application No. 61/123,384, filed on Apr. 8, 2008, provisional application No. 61/068,130, filed on Mar. 4, 2008, provisional application No. 61/123,417, filed on Apr. 8, 2008, provisional application No. 61/123,412, filed on Apr. 8, 2008, provisional application No. 61/126,830, filed on May 7, 2008, provisional application No. 61/126,620, filed on May 6, 2008.

(56) References Cited

U.S. PATENT DOCUMENTS

| | | |
|---|---|---|
| 1,719,750 A | 9/1927 | Bridge et al. |
| 3,818,913 A | 6/1974 | Wallach |
| 3,880,168 A | 4/1975 | Berman |
| 3,930,505 A | 1/1976 | Wallach |
| 4,024,866 A | 5/1977 | Wallach |
| 4,083,077 A | 4/1978 | Knight et al. |
| 4,447,227 A | 5/1984 | Kotsanis |
| 4,672,962 A | 6/1987 | Hershenson |
| 4,682,596 A | 7/1987 | Bales et al. |
| 4,748,979 A | 6/1988 | Hershenson |
| 4,773,410 A | 9/1988 | Blackmer et al. |
| 4,793,352 A | 12/1988 | Eichenlaub |
| 4,872,915 A | 10/1989 | Flynn et al. |
| 4,898,574 A | 2/1990 | Uchiyama et al. |
| 4,915,113 A | 4/1990 | Holman |
| 4,941,475 A | 7/1990 | Williams et al. |
| 4,950,266 A | 8/1990 | Sinofsky |
| 4,985,027 A | 1/1991 | Dressel |
| 5,006,119 A | 4/1991 | Acker et al. |
| 5,011,566 A | 4/1991 | Hoffman |
| 5,078,736 A | 1/1992 | Behl |
| 5,084,043 A | 1/1992 | Hertzmann et al. |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,263,951 A | 11/1993 | Spears et al. |
| 5,277,696 A | 1/1994 | Hagen |
| 5,298,298 A | 3/1994 | Hoffman |
| 5,306,274 A | 4/1994 | Long |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,462,521 A | 10/1995 | Brucker et al. |
| 5,500,012 A | 3/1996 | Brucker et al. |
| 5,503,638 A | 4/1996 | Cooper et al. |
| 5,505,730 A | 4/1996 | Edwards |
| 5,524,620 A | 6/1996 | Rosenschein |
| 5,529,076 A | 6/1996 | Schachar |
| 5,542,928 A | 8/1996 | Evans et al. |
| 5,549,628 A | 8/1996 | Cooper et al. |
| 5,554,172 A | 9/1996 | Horner et al. |
| 5,562,608 A | 10/1996 | Sekins et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,647,871 A | 7/1997 | Levine et al. |
| 5,653,692 A | 8/1997 | Masterson et al. |
| 5,662,671 A | 9/1997 | Barbut et al. |
| 5,669,907 A | 9/1997 | Platt, Jr. et al. |
| 5,681,282 A | 10/1997 | Eggers et al. |
| 5,683,366 A | 11/1997 | Eggers et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,735,811 A | 4/1998 | Brisken |
| 5,741,247 A | 4/1998 | Rizoiu et al. |
| 5,741,248 A | 4/1998 | Stern et al. |
| 5,752,965 A | 5/1998 | Francis et al. |
| 5,755,753 A | 5/1998 | Knowlton |
| 5,769,880 A | 6/1998 | Truckai et al. |
| 5,782,914 A | 7/1998 | Schankereli |
| 5,785,521 A | 7/1998 | Rizoiu et al. |
| 5,800,482 A | 9/1998 | Pomeranz et al. |
| 5,810,764 A | 9/1998 | Eggers et al. |
| 5,824,703 A | 10/1998 | Clark, Jr. |
| 5,827,268 A | 10/1998 | Laufer |
| 5,836,896 A | 11/1998 | Rosenschein |
| 5,843,019 A | 12/1998 | Eggers et al. |
| 5,843,073 A | 12/1998 | Sinofsky |
| 5,871,469 A | 2/1999 | Eggers |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,911,734 A | 6/1999 | Tsugita et al. |
| 5,913,856 A | 6/1999 | Chia et al. |
| 5,938,660 A | 8/1999 | Swartz et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwin |
| 5,989,445 A | 11/1999 | Wise et al. |
| 5,997,499 A | 12/1999 | Sussman et al. |
| 6,024,095 A | 2/2000 | Stanley, III |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,047,700 A | 4/2000 | Eggers et al. |
| 6,053,909 A | 4/2000 | Shadduck |
| 6,056,746 A | 5/2000 | Goble et al. |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,066,139 A | 5/2000 | Ryan et al. |
| 6,074,358 A | 6/2000 | Andrew et al. |
| 6,080,128 A | 6/2000 | Sussman et al. |
| 6,080,151 A | 6/2000 | Swartz et al. |
| 6,083,255 A | 7/2000 | Laufer et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,106,516 A | 8/2000 | Bmassengill |
| 6,110,162 A | 8/2000 | Sussman et al. |
| 6,113,722 A | 9/2000 | Hoffman et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,194 A | 12/2000 | Eggers et al. |

(56) References Cited

U.S. PATENT DOCUMENTS

| | | |
|---|---|---|
| 6,162,232 A | 12/2000 | Shadduck |
| 6,168,594 B1 | 1/2001 | LaFontaine et al. |
| 6,174,308 B1 | 1/2001 | Goble et al. |
| 6,179,805 B1 | 1/2001 | Sussman et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,206,848 B1 | 3/2001 | Sussman et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,654 B1 | 7/2001 | Swartz et al. |
| 6,277,112 B1 | 8/2001 | Underwood et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,296,636 B1 | 10/2001 | Cheng et al. |
| 6,296,638 B1 | 10/2001 | Davidson et al. |
| 6,299,633 B1 | 10/2001 | Laufer |
| 6,300,150 B1 | 10/2001 | Venkatasubramanian |
| 6,312,408 B1 | 11/2001 | Eggers et al. |
| 6,312,474 B1 | 11/2001 | Francis et al. |
| 6,315,755 B1 | 11/2001 | Sussman |
| 6,319,222 B1 | 11/2001 | Andrew et al. |
| 6,327,505 B1 | 12/2001 | Medhkour et al. |
| 6,331,171 B1 | 12/2001 | Cohen |
| 6,355,032 B1 | 3/2002 | Hovda et al. |
| 6,375,635 B1 | 4/2002 | Moutafis et al. |
| 6,379,350 B1 | 4/2002 | Sharkey et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,416,508 B1 | 7/2002 | Eggers et al. |
| 6,458,231 B1 | 10/2002 | Wapner et al. |
| 6,461,350 B1 | 10/2002 | Underwood et al. |
| 6,464,694 B1 | 10/2002 | Massengil |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,475,215 B1 | 11/2002 | Tanrisever |
| 6,482,201 B1 | 11/2002 | Olsen et al. |
| 6,482,202 B1 | 11/2002 | Goble et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,517,533 B1 | 2/2003 | Swaminathan |
| 6,517,568 B1 | 2/2003 | Sharkey et al. |
| 6,522,930 B1 | 2/2003 | Schaer et al. |
| 6,527,761 B1 | 3/2003 | Soltesz et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,248 B1 | 4/2003 | Bass |
| 6,547,810 B1 | 4/2003 | Sharkey et al. |
| 6,558,379 B1 | 5/2003 | Batchelor et al. |
| 6,569,146 B1 | 5/2003 | Werner et al. |
| 6,575,929 B2 | 6/2003 | Sussman et al. |
| 6,575,933 B1 | 6/2003 | Wittenberger et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,204 B1 | 7/2003 | Sussman et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,605,087 B2 | 8/2003 | Swartz et al. |
| 6,610,043 B1 | 8/2003 | Ingenito |
| 6,620,130 B1 | 9/2003 | Ginsburg |
| 6,620,155 B2 | 9/2003 | Underwood et al. |
| 6,623,444 B2 | 9/2003 | Babaev |
| 6,632,193 B1 | 10/2003 | Davison et al. |
| 6,632,220 B1 | 10/2003 | Eggers et al. |
| 6,634,363 B1 | 10/2003 | Danek et al. |
| 6,648,847 B2 | 11/2003 | Sussman et al. |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,682,520 B2 | 1/2004 | Ingenito |
| 6,682,543 B2 | 1/2004 | Barbut et al. |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,723,064 B2 | 4/2004 | Babaev |
| 6,726,684 B1 | 4/2004 | Woloszko et al. |
| 6,726,708 B2 | 4/2004 | Lasheras |
| 6,746,447 B2 | 6/2004 | Davison et al. |
| 6,755,794 B2 | 6/2004 | Soukup |
| 6,758,846 B2 | 7/2004 | Goble et al. |
| 6,763,836 B2 | 7/2004 | Novak et al. |
| 6,764,487 B2 | 7/2004 | Mulier et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,813,520 B2 | 11/2004 | Truckai et al. |
| 6,832,996 B2 | 12/2004 | Woloszko et al. |
| 6,837,884 B2 | 1/2005 | Woloszko |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B1 | 3/2005 | Sussman et al. |
| 6,875,194 B2 | 4/2005 | MacKool |
| 6,896,674 B1 | 5/2005 | Wolosko et al. |
| 6,896,675 B2 | 5/2005 | Leung et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,918,903 B2 | 7/2005 | Bass |
| 6,921,385 B2 | 7/2005 | Clements et al. |
| 6,929,640 B1 | 8/2005 | Underwood et al. |
| 6,949,096 B2 | 9/2005 | Davison et al. |
| 6,955,675 B2 | 10/2005 | Jain |
| 6,960,182 B2 | 11/2005 | Moutafis et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |

(56) References Cited

U.S. PATENT DOCUMENTS

| | | |
|---|---|---|
| 6,991,028 B2 | 1/2006 | Comeaux et al. |
| 6,991,631 B2 | 1/2006 | Wolosko et al. |
| 7,022,088 B2 | 4/2006 | Keast et al. |
| 7,031,504 B1 | 4/2006 | Argiro et al. |
| 7,083,612 B2 | 8/2006 | Littrup et al. |
| 7,094,249 B1 | 8/2006 | Broome et al. |
| 7,128,748 B2 | 10/2006 | Mooradian et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,162,303 B2 | 1/2007 | Levin et al. |
| 7,192,400 B2 | 3/2007 | Campbell et al. |
| 7,233,820 B2 | 6/2007 | Gilboa |
| 7,235,070 B2 | 6/2007 | Vanney |
| 7,311,708 B2 | 12/2007 | McClurken |
| 7,335,195 B2 | 2/2008 | Mehier |
| 7,347,859 B2 | 3/2008 | Garabedian et al. |
| 7,524,315 B2 | 4/2009 | Blott et al. |
| 7,549,987 B2 | 6/2009 | Shadduck |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,674,259 B2 | 3/2010 | Shadduck |
| 7,717,948 B2 | 5/2010 | Demarais et al. |
| 7,756,583 B2 | 7/2010 | Demarais et al. |
| 7,815,616 B2 | 10/2010 | Boehringer et al. |
| 7,815,646 B2 | 10/2010 | Hart |
| 7,853,333 B2 | 12/2010 | Demarais |
| 7,873,417 B2 | 1/2011 | Demarais et al. |
| 7,892,229 B2 | 2/2011 | Shadduck et al. |
| 7,937,143 B2 | 5/2011 | Demarais et al. |
| 7,993,323 B2 | 8/2011 | Barry et al. |
| 8,016,823 B2 | 9/2011 | Shadduck |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,269 B2 | 5/2012 | Shadduck et al. |
| 8,192,424 B2 | 6/2012 | Woloszko |
| 8,313,485 B2 | 11/2012 | Shadduck |
| 8,444,636 B2 | 5/2013 | Shadduck et al. |
| 8,574,226 B2 | 11/2013 | Shadduck |
| 8,579,888 B2 | 11/2013 | Hoey et al. |
| 8,579,892 B2 | 11/2013 | Hoey et al. |
| 8,579,893 B2 | 11/2013 | Hoey |
| 9,113,944 B2 | 8/2015 | Shadduck |
| 2001/0020167 A1 | 9/2001 | Woloszko et al. |
| 2001/0029370 A1 | 10/2001 | Hodva et al. |
| 2001/0037106 A1 | 11/2001 | Shadduck |
| 2002/0049438 A1 | 4/2002 | Sharkey et al. |
| 2002/0077516 A1 | 6/2002 | Flanigan |
| 2002/0078956 A1* | 6/2002 | Sharpe et al. ............ 128/203.26 |
| 2002/0082667 A1 | 6/2002 | Shadduck |
| 2002/0095152 A1 | 7/2002 | Ciarrocca et al. |
| 2002/0111386 A1 | 8/2002 | Sekins et al. |
| 2002/0128638 A1 | 9/2002 | Chauvet et al. |
| 2002/0133148 A1* | 9/2002 | Daniel et al. ............... 606/34 |
| 2002/0151917 A1 | 10/2002 | Barry |
| 2002/0161326 A1 | 10/2002 | Sussman et al. |
| 2002/0173815 A1 | 11/2002 | Hogendijk et al. |
| 2002/0177846 A1* | 11/2002 | Mulier et al. ............... 606/27 |
| 2002/0193789 A1 | 12/2002 | Underwood et al. |
| 2003/0028189 A1 | 2/2003 | Woloszko et al. |
| 2003/0040742 A1 | 2/2003 | Underwood et al. |
| 2003/0097126 A1 | 5/2003 | Woloszko et al. |
| 2003/0097129 A1 | 5/2003 | Davison et al. |
| 2003/0099279 A1 | 5/2003 | Venkatasubramanian et al. |
| 2003/0109869 A1 | 6/2003 | Shadduck |
| 2003/0130655 A1 | 7/2003 | Woloszko et al. |
| 2003/0130738 A1 | 7/2003 | Hovda et al. |
| 2003/0144654 A1 | 7/2003 | Hilal |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1* | 11/2003 | Pearson et al. ............... 606/41 |
| 2003/0212395 A1 | 11/2003 | Woloszko et al. |
| 2003/0225364 A1 | 12/2003 | Kraft et al. |
| 2004/0024398 A1 | 2/2004 | Hovda et al. |
| 2004/0024399 A1 | 2/2004 | Sharps et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0049180 A1 | 3/2004 | Sharps et al. |
| 2004/0054366 A1 | 3/2004 | Davison et al. |
| 2004/0055606 A1 | 3/2004 | Hendricksen et al. |
| 2004/0068256 A1 | 4/2004 | Rizoiu et al. |
| 2004/0068306 A1 | 4/2004 | Shadduck |
| 2004/0087937 A1 | 5/2004 | Eggers et al. |
| 2004/0116922 A1 | 6/2004 | Hovda et al. |
| 2004/0193150 A1 | 9/2004 | Sharkey et al. |
| 2004/0199226 A1 | 10/2004 | Shadduck |
| 2004/0230190 A1 | 11/2004 | Dahla et al. |
| 2004/0254532 A1 | 12/2004 | Mehier |
| 2005/0004634 A1 | 1/2005 | Ricart et al. |
| 2005/0010205 A1 | 1/2005 | Hovda et al. |
| 2005/0070894 A1 | 3/2005 | McClurken |
| 2005/0119650 A1 | 6/2005 | Sanders et al. |
| 2005/0166925 A1 | 8/2005 | Wilson et al. |
| 2005/0171582 A1 | 8/2005 | Matlock |
| 2005/0187543 A1 | 8/2005 | Underwood et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0267467 A1 | 12/2005 | Paul et al. |
| 2005/0267468 A1 | 12/2005 | Truckai et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0085054 A1* | 4/2006 | Zikorus et al. ............... 607/96 |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161233 A1 | 7/2006 | Barry et al. |
| 2006/0200076 A1 | 9/2006 | Gonzalez et al. |
| 2006/0206150 A1 | 9/2006 | Demarais et al. |
| 2006/0224154 A1 | 10/2006 | Shadduck et al. |
| 2006/0271111 A1 | 11/2006 | Demarais et al. |
| 2007/0032785 A1 | 2/2007 | Diederich et al. |
| 2007/0036417 A1 | 2/2007 | Argiro et al. |
| 2007/0091087 A1 | 4/2007 | Zuiderveld |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0265687 A1 | 11/2007 | Deem et al. |
| 2008/0033493 A1 | 2/2008 | Deckman et al. |
| 2008/0077201 A1 | 3/2008 | Levinson et al. |
| 2008/0097429 A1 | 4/2008 | McClurken |
| 2008/0103566 A1 | 5/2008 | Mehier |
| 2008/0110457 A1 | 5/2008 | Barry et al. |
| 2008/0114297 A1 | 5/2008 | Barry et al. |
| 2008/0125747 A1 | 5/2008 | Prokop |
| 2008/0132826 A1 | 6/2008 | Shadduck et al. |
| 2008/0213331 A1 | 9/2008 | Gelfand et al. |
| 2008/0255642 A1 | 10/2008 | Zarins et al. |
| 2009/0030412 A1 | 1/2009 | Willis et al. |
| 2009/0036948 A1 | 2/2009 | Levin et al. |
| 2009/0054871 A1 | 2/2009 | Sharkey et al. |
| 2009/0062873 A1 | 3/2009 | Wu et al. |
| 2009/0076409 A1 | 3/2009 | Wu et al. |
| 2009/0105702 A1 | 4/2009 | Shadduck |
| 2009/0105703 A1 | 4/2009 | Shadduck |
| 2009/0125009 A1 | 5/2009 | Zikorus et al. |
| 2009/0149846 A1 | 6/2009 | Hoey et al. |
| 2009/0306640 A1 | 12/2009 | Glaze et al. |

(56) References Cited

U.S. PATENT DOCUMENTS

| | | |
|---|---|---|
| 2009/0312753 A1 | 12/2009 | Shadduck |
| 2010/0076416 A1 | 3/2010 | Hoey et al. |
| 2010/0094270 A1 | 4/2010 | Sharma |
| 2010/0114083 A1 | 5/2010 | Sharma |
| 2010/0137860 A1 | 6/2010 | Demarais et al. |
| 2010/0137952 A1 | 6/2010 | Demarais et al. |
| 2010/0160905 A1 | 6/2010 | Shadduck |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |
| 2010/0185189 A1 | 7/2010 | Hoey |
| 2010/0191112 A1 | 7/2010 | Demarais et al. |
| 2010/0204688 A1 | 8/2010 | Hoey et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0262133 A1 | 10/2010 | Hoey et al. |
| 2010/0268307 A1 | 10/2010 | Demarais et al. |
| 2011/0060324 A1 | 3/2011 | Wu et al. |
| 2011/0077628 A1 | 3/2011 | Hoey et al. |
| 2011/0112400 A1 | 5/2011 | Emery et al. |
| 2011/0118717 A1 | 5/2011 | Shadduck |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0203096 A1 | 8/2011 | Demarais et al. |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0172837 A1 | 7/2012 | Demarais et al. |
| 2012/0197198 A1 | 8/2012 | Demarais et al. |
| 2012/0197252 A1 | 8/2012 | Deem et al. |
| 2012/0259271 A1 | 10/2012 | Shadduck et al. |
| 2013/0079772 A1 | 3/2013 | Shadduck |
| 2013/0116683 A1 | 5/2013 | Shadduck et al. |
| 2013/0237978 A1 | 9/2013 | Shadduck et al. |
| 2014/0018890 A1 | 1/2014 | Hoey et al. |
| 2014/0025057 A1 | 1/2014 | Hoey et al. |
| 2014/0031805 A1 | 1/2014 | Shadduck |

FOREIGN PATENT DOCUMENTS

| | | |
|---|---|---|
| WO | WO 2002/069821 | 9/2002 |
| WO | WO 2003/070302 | 8/2003 |
| WO | WO 2003/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

U.S. Appl. No. 09/181,906, filed Oct. 28, 1998, in the name of Shadduck, Non-Final Rejection dated Mar. 15, 2000.

U.S. Appl. No. 09/181,906, filed Oct. 28, 1998, in the name of Shadduck, Notice of Allowance dated Sep. 26, 2000.

U.S. Appl. No. 09/281,493, filed Mar. 30, 1999 in the name of Shadduck, entitled "Ionothermal system and technique for dermal treatments".

U.S. Appl. No. 09/557,931, filed Apr. 22, 2000 in the name of Shadduck, entitled "Ionothermal delivery system and technique for medical procedures".

U.S. Appl. No. 09/580,767, filed May 30, 2000 in the name of Shadduck, entitled "Microjoule electrical discharge catheter for thrombolysis in the stroke patients".

U.S. Appl. No. 09/782,649, filed Feb. 12, 2001, in the name of Shadduck, Notice of Allowance dated Sep. 9, 2002.

U.S. Appl. No. 10/017,582, filed Dec. 7, 2001, in the name of Shadduck, Non-Final Rejection dated Dec. 10, 2002.

U.S. Appl. No. 10/017,582, filed Dec. 7, 2001, in the name of Shadduck, Non-Final Rejection dated Jul. 17, 2003.

U.S. Appl. No. 10/346,877, filed Jan. 18, 2003, in the name of Shadduck, Examiner's Amendment dated Mar. 7, 2005.

U.S. Appl. No. 10/346,877, filed Jan. 18, 2003, in the name of Shadduck, Non-Final Rejection dated Sep. 30, 2004.

U.S. Appl. No. 10/346,877, filed Jan. 18, 2003, in the name of Shadduck, Notice of Allowance dated Mar. 7, 2005.

U.S. Appl. No. 10/681,625, filed Oct. 7, 2003, in the name of Shadduck, Final Rejection dated Jun. 3, 2008.

U.S. Appl. No. 10/681,625, filed Oct. 7, 2003, in the name of Shadduck, Non-Final Rejection dated Aug. 15, 2007.

U.S. Appl. No. 10/681,625, filed Oct. 7, 2003, in the name of Shadduck, Non-Final Rejection dated Mar. 13, 2009.

U.S. Appl. No. 10/681,625, filed Oct. 7, 2003, in the name of Shadduck, Notice of Allowance dated Dec. 30, 2009.

U.S. Appl. No. 11/158,930, filed Jun. 22, 2005, in the name of Shadduck, Non-Final Rejection dated Jun. 24, 2009.

U.S. Appl. No. 11/244,329, filed Jan. 18, 2003, in the name of Shadduck, Non-Final Rejection dated Jun. 19, 2009.

U.S. Appl. No. 12/465,927, filed May 14, 2009, in the name of Shadduck, entitled "Thermotherapy device".

Coda, et al., "Effects of pulmonary reventilation on gas exchange after cryolytic disobstruction of endobronchial tumors," *Minerva Medical*, vol. 72, pp. 1627-1631, Jun. 1981 (with English translation).

Fishman et al., "A randomized trial comparing lung-volume-reduction surgery with medical therapy for severe emphysema," *N Engl J Med*, vol. 348, No. 21, pp. 2059-2073, May 22, 2003.

Homasson, et al., "Bronchoscopic cryotherapy for airway strictures caused by tumors," *Chest*, vol. 90, No. 2, pp. 159-164, Aug. 1986.

Li, K., "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," *Chest*, vol. 103, No. 2, pp. 472-474, Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction." *Chest*, vol. 110, No. 3, pp. 718-723, Sep. 1996.

Morice et al. "Endobrinchial argon plasma coagulation for treatment of hemotysis and neoplastic airway obstruction," *Chest*, vol. 119, No. 3, pp. 781-787, Mar. 2001.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp. 1-17, 1994.

Tschirren et al.; "Intrathoracic airway trees: segmentation and airway morphology analysis from low-dose CT scans;" *IEEE Trans. Med. Imaging*, vol. 24, No. 12; pp. 1529-1539, Dec. 2005.

(56) References Cited

OTHER PUBLICATIONS

Tschirren, J., "Segmentation, anatomical labeling, branchpoint matching, and quantitative analysis of human airway trees in volumetric CT images," Ph.D. Thesis, The University of Iowa, 231 pages, Aug. 2003.
Tschirren, J., "Segmentation, anatomical labeling, branchpoint matching, and quantitative analysis of human airway trees in volumetric CT images," Slides from Ph.D. defense, University of Iowa, 130 pages, Aug. 2003.
Unger, M. et al. "Monolithic Microfabricated Valves and Pumps by Multilayer Soft Lithography," *Science*, vol. 288, pp. 113-116, Apr. 7, 2000, accessed at http://web.mit.edu/thorsen/www/113.pdf.

\* cited by examiner

MEDICAL SYSTEM AND METHOD OF USE

CROSS-REFERENCE TO RELATED APPLICATIONS

This application is a non-provisional of U.S. Provisional Application No. 61/126,647 Filed on May 6, 2008 MEDICAL SYSTEM AND METHOD OF USE; Application No. 61/126,651 Filed on May 6, 2008 MEDICAL SYSTEM AND METHOD OF USE; Application No. 61/126,612 Filed on May 6, 2008 MEDICAL SYSTEM AND METHOD OF USE; Application No. 61/126,636 Filed on May 6, 2008 MEDICAL SYSTEM AND METHOD OF USE; Application No. 61/130,345 Filed on May 31, 2008 MEDICAL SYSTEM AND METHOD OF USE; Application No. 61/191,459 Filed on Sep. 9, 2008 MEDICAL SYSTEM AND METHOD OF USE; Application No. 61/066,396 Filed on Feb. 20, 2008 TISSUE ABLATION SYSTEM AND METHOD OF USE; Application No. 61/123,416 Filed on Apr. 8, 2008 MEDICAL SYSTEM AND METHOD OF USE; Application No. 61/068,049 Filed on Mar. 4, 2008 MEDICAL SYSTEM AND METHOD OF USE; Application No. 61/123,384 Filed on Apr. 8, 2008 MEDICAL SYSTEM AND METHOD OF USE; Application No. 61/068,130 Filed on Mar. 4, 2008 MEDICAL SYSTEM AND METHOD OF USE; Application No. 61/123,417 Filed on Apr. 8, 2008 MEDICAL SYSTEM AND METHOD OF USE; Application No. 61/123,412 Filed on Apr. 8, 2008 MEDICAL SYSTEM AND METHOD OF USE; Application No. 61/126,830 Filed on May 7, 2008 MEDICAL SYSTEM AND METHOD OF USE; and Application No. 61/126,620 Filed on May 6, 2008 MEDICAL SYSTEM AND METHOD OF USE.

The systems and methods described herein are also related to U.S. patent application Ser. No. 10/681,625 filed Oct. 7, 2003 titled "Medical Instruments and Techniques for Thermally-Mediated Therapies"; Ser. No. 11/158,930 filed Jun. 22, 2005 titled "Medical Instruments and Techniques for Treating Pulmonary Disorders"; Ser. No. 11/244,329 filed Oct. 5, 2005 titled "Medical Instruments and Methods of Use" and Ser. No. 11/329,381 filed Jan. 10, 2006 titled "Medical Instrument and Method of Use".

All of the above applications are incorporated herein by this reference and made a part of this specification, together with the specifications of all other commonly-invented applications cited in the above applications.

FIELD OF THE INVENTION

This invention relates to medical instruments and systems for applying energy to tissue, and more particularly relates to a system for ablating, sealing, welding, coagulating, shrinking or creating lesions in tissue by means of contacting a targeted tissue in a patient with a vapor phase media wherein a subsequent vapor-to-liquid phase change of the media applies thermal energy to the tissue to cause an intended therapeutic effect. Variations of the invention include devices and methods for generating a flow of high quality vapor and monitoring the vapor flow for various parameters with one or more sensors. In yet additional variations, the invention includes devices and methods for modulating parameters of the system in response to the observed parameters.

BACKGROUND OF THE INVENTION

What is needed is systems and methods that controllably apply thermal energy in a controlled and localized manner without the lack of control often associated when Rf, laser and microwave energy are applied directly to tissue.

What is needed is are systems and methods that controllably apply thermal energy in a controlled and localized manner without the lack of control often associated when Rf, laser and microwave energy are applied directly to tissue.

SUMMARY OF THE INVENTION

The present invention is adapted to provide improved methods of controlled thermal energy delivery to localized tissue volumes, for example for ablating, sealing, coagulating or otherwise damaging targeted tissue, for example to ablate a tissue volume interstitially or to ablate the lining of a body cavity. Of particular interest, the method causes thermal effects in targeted tissue without the use of Rf current flow through the patient's body and without the potential of carbonizing tissue.

In general, the thermally-mediated treatment method comprises causing a vapor-to-liquid phase state change in a selected media at a targeted tissue site thereby applying thermal energy substantially equal to the heat of vaporization of the selected media to the tissue site. The thermally-mediated therapy can be delivered to tissue by such vapor-to-liquid phase transitions, or "internal energy" releases, about the working surfaces of several types of instruments for ablative treatments of soft tissue. FIGS. 1A and 1B illustrate the phenomena of phase transitional releases of internal energies. Such internal energy involves energy on the molecular and atomic scale—and in polyatomic gases is directly related to intermolecular attractive forces, as well as rotational and vibrational kinetic energy. In other words, the method of the invention exploits the phenomenon of internal energy transitions between gaseous and liquid phases that involve very large amounts of energy compared to specific heat.

It has been found that the controlled application of such energy in a controlled media-tissue interaction solves many of the vexing problems associated with energy-tissue interactions in Rf, laser and ultrasound modalities. The apparatus of the invention provides a vaporization chamber in the interior of an instrument, in an instrument working end or in a source remote from the instrument end. A source provides liquid media to the interior vaporization chamber wherein energy is applied to create a selected volume of vapor media. In the process of the liquid-to-vapor phase transition of a liquid media, for example water, large amounts of energy are added to overcome the cohesive forces between molecules in the liquid, and an additional amount of energy is required to expand the liquid 1000+ percent (PΔD) into a resulting vapor phase (see FIG. 1A). Conversely, in the vapor-to-liquid transition, such energy will be released at the phase transition at the interface with the targeted tissue site. That is, the heat of vaporization is released at the interface when the media transitions from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy at the interface with the targeted body structure. Heat flow and work are both ways of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calories/gm blocks) to elevate the temperature of water through its phase change to a vapor phase, the additional energy required to achieve the phase change (latent heat of vaporization) is represented by the large number of 110+ blocks of energy at 100° C. in FIG. 1A. Still referring to FIG. 1A, it can be easily understood that all other prior art ablation modalities—Rf, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present invention. The system provides for insulative containment of an initial primary energy-media interaction within an interior vaporization chamber of medical thermotherapy system. The initial, ascendant energy-media interaction delivers energy sufficient to achieve the heat of vaporization of a selected liquid media, such as water or saline solution, within an interior of the system. This aspect of the technology requires a highly controlled energy source wherein a computer controller may need to modulated energy application between very large energy densities to initially surpass the latent heat of vaporization with some energy sources (e.g. a resistive heat source, an Rf energy source, a light energy source, a microwave energy source, an ultrasound source and/or an inductive heat source) and potential subsequent lesser energy densities for maintaining a high vapor quality. Additionally, a controller must control the pressure of liquid flows for replenishing the selected liquid media at the required rate and optionally for controlling propagation velocity of the vapor phase media from the working end surface of the instrument. In use, the method of the invention comprises the controlled application of energy to achieve the heat of vaporization as in FIG. 1A and the controlled vapor-to-liquid phase transition and vapor exit pressure to thereby control the interaction of a selected volume of vapor at the interface with tissue. The vapor-to-liquid phase transition can deposit 400, 500, 600 or more cal/gram within the targeted tissue site to perform the thermal ablation with the vapor in typical pressures and temperatures.

In one variation, the present disclosure includes medical systems for applying thermal energy to tissue, where the system comprises an elongated probe with an axis having an interior flow channel extending to at least one outlet in a probe working end; a source of vapor media configured to provide a vapor flow through at least a portion of the interior flow channel, wherein the vapor has a minimum temperature; and at least one sensor in the flow channel for providing a signal of at least one flow parameter selected from the group one of (i) existence of a flow of the vapor media, (ii) quantification of a flow rate of the vapor media, and (iii) quality of the flow of the vapor media. The medical system can include variations where the minimum temperature varies from at least 80° C., 100° C. 120° C., 140° C. and 160° C. However, other temperature ranges can be included depending upon the desired application.

Sensors included in the above system include temperature sensor, an impedance sensor, a pressure sensor as well as an optical sensor.

The source of vapor media can include a pressurized source of a liquid media and an energy source for phase conversion of the liquid media to a vapor media. In addition, the medical system can further include a controller capable of modulating a vapor parameter in response to a signal of a flow parameter; the vapor parameter selected from the group of (i) flow rate of pressurized source of liquid media, (ii) inflow pressure of the pressurized source of liquid media, (iii) temperature of the liquid media, (iv) energy applied from the energy source to the liquid media, (v) flow rate of vapor media in the flow channel, (vi) pressure of the vapor media in the flow channel, (vi) temperature of the vapor media, and (vii) quality of vapor media.

In another variation, a novel medical system for applying thermal energy to tissue comprises an elongated probe with an axis having an interior flow channel extending to at least one outlet in a probe working end, wherein a wall of the flow channel includes an insulative portion having a thermal conductivity of less than a maximum thermal conductivity; and a source of vapor media configured to provide a vapor flow through at least a portion of the interior flow channel, wherein the vapor has a minimum temperature.

Variations of such systems include systems where the maximum thermal conductivity ranges from 0.05 W/mK, 0.01 W/mK and 0.005 W/mK.

Methods are disclosed herein for thermally treating tissue by providing a probe body having a flow channel extending therein to an outlet in a working end, introducing a flow of a liquid media through the flow channel and applying energy to the tissue by inductively heating a portion of the probe sufficient to vaporize the flowing media within the flow channel causing pressurized ejection of the media from the outlet to the tissue.

The methods can include applying energy between 10 and 400,000 Joules to the tissue from the media. The rate at which the media flows can be controlled as well.

Introducing the flow of liquid media can further include introducing the flow of liquid media in less than 10 minutes. However, the rate can be reduced as described below.

In another variation, the methods described herein include inductively heating the portion of the probe by applying an electromagnetic energy source to a coil surrounding the flow channel. The electromagnetic energy can also inductively heat a wall portion of the flow channel.

Another variation of the method includes providing a flow permeable structure within the flow channel. Optionally, the coil described herein can heat the flow permeable structure to transfer energy to the flow media. Some examples of a flow permeable structure include woven filaments, braided filaments, knit filaments, metal wool, a microchannel structure, a porous structure, a honeycomb structure and an open cell structure. However, any structure that is permeable to flow can be included.

The electromagnetic energy source can include an energy source ranging from a 10 Watt source to a 500 Watt source.

Medical systems for treating tissue are also described herein. Such systems can include a probe body having a flow channel extending therein to an outlet in a working end, a coil about at least a portion or the flow channel, and an electromagnetic energy source coupled to the coil, where the electromagnetic energy source induces current in the coil causing energy delivery to a flowable media in the flow channel. The systems can include a source of flowable media coupled to the flow channel. The electromagnetic energy source can be capable of applying energy to the flowable media sufficient to cause a liquid-to-vapor phase change in at least a portion of the flowable media as described in detail herein. In addition the probe can include a sensor selected from a temperature sensor, an impedance sensor, a capacitance sensor and a pressure sensor. In some variations the probe is coupled to an aspiration source.

The medical system can also include a controller capable of modulating at least one operational parameter of the source of flowable media in response to a signal from a sensor. For example, the controller can be capable of modulating a flow of the flowable media. In another variation, the controller is capable of modulating a flow of the flowable media to apply between 100 and 400,000 Joules to the tissue.

The systems described herein can also include a metal portion in the flow channel for contacting the flowable media. The metal portion can be a flow permeable stricture and can optionally comprise a microchannel structure. In additional variations, the flow permeable structure can include woven filaments, braided filaments, knit filaments, metal wool, a porous structure, a honeycomb structure, an open cell structure or a combination thereof.

In another variation, the methods described herein can include positioning a probe in an interface with a targeted tissue, and causing a vapor media to be ejected from the probe into the interface with tissue wherein the media delivers energy ranging from 5 joules to 400,000 joules to cause a therapeutic effect, wherein the vapor media is converted from a liquid media within the probe by inductive heating means.

Methods described herein also include methods of treating tissue by providing medical system including a heat applicator portion for positioning in an interface with targeted tissue, and converting a liquid media into a vapor media within an elongated portion of the medical system having a flow channel communicating with a flow outlet in the heat applicator portion, and contacting the vapor media with the targeted tissue to thereby deliver energy ranging from 5 joules to 100,000 joules to cause a therapeutic effect.

As discussed herein, the methods can include converting the liquid into a vapor media using an inductive heating means. In an alternate variation, a resistive heating means can be combined with the inductive heating means or can replace the inductive heating means.

The instrument and method of the invention can cause an energy-tissue interaction that is imagable with intra-operative ultrasound or MRI.

The instrument and method of the invention cause thermal effects in tissue that do not rely applying an electrical field across the tissue to be treated.

Additional advantages of the invention will be apparent from the following description, the accompanying drawings and the appended claims.

All patents, patent applications and publications mentioned in this specification are herein incorporated by reference to the same extent as if each individual publication or patent application was specifically and individually indicated to be incorporated by reference.

In addition, it is intended that combinations of aspects of the systems and methods described herein as well as the various embodiments themselves, where possible, are within the scope of this disclosure.

DETAILED DESCRIPTION OF THE INVENTION

As used in the specification, "a" or "an" means one or more. As used in the claim(s), when used in conjunction with the word "comprising", the words "a" or "an" mean one or more. As used herein, "another" means as least a second or more. "Substantially" or "substantial" mean largely but not entirely. For example, substantially may mean about 10% to about 99.999, about 25% to about 99.999% or about 50% to about 99.999%.

Treatment Liquid Source, Energy Source, Controller

Figure 2:
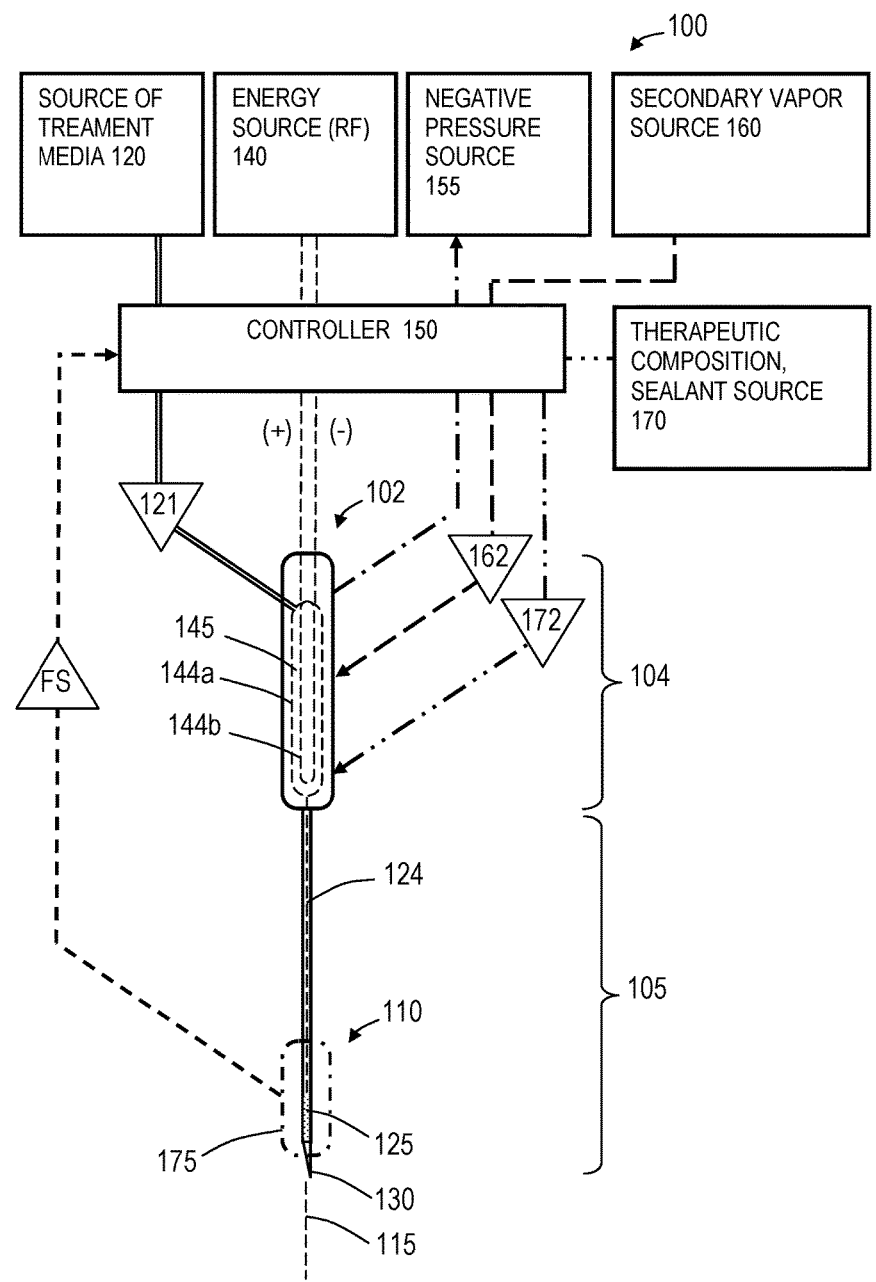
FIG. 2 is a schematic view of thermotherapy medical system adapted for treating tissue.

Referring to FIG. 2, a schematic view of medical system 100 of the present invention is shown that is adapted for treating a tissue target, wherein the treatment comprises an ablation or thermotherapy and the tissue target can comprise any mammalian soft tissue to be ablated, sealed, contracted, coagulated, damaged or treated to elicit an immune response. The system 100 include an instrument or probe body 102 with a proximal handle end 104 and an extension portion 105 having a distal or working end indicated at 110. In one embodiment depicted in FIG. 2, the handle end 104 and extension portion 105 generally extend about longitudinal axis 115. In the embodiment of FIG. 2, the extension portion 105 is a substantially rigid tubular member with at least one flow channel therein, but the scope of the invention encompasses extension portions 105 of any mean diameter and any axial length, rigid or flexible, suited for treating a particular tissue target. In one embodiment, a rigid extension portion 105 can comprise a 20 Ga. to 40 Ga. needle with a short length for thermal treatment of a patient's cornea or a somewhat longer length for treating tissue underlying a patient's retina. In another embodiment, an elongate extension portion 105 of a vapor delivery tool can comprise a single needle or a plurality of needles having suitable lengths for tumor or soft tissue ablation in a liver, breast, gall bladder, prostate, bone and the like. In another embodiment, an elongate extension portion 105 can comprise a flexible catheter for introduction through a body lumen to access at tissue target, with a diameter ranging from about 1 to 10 mm. In another embodiment, the extension portion 105 or working end 110 can be articulatable, deflectable or deformable. The probe handle end 104 can be configured as a hand-held member, or can be configured for coupling to a robotic surgical system. In another embodiment, the working end 110 carries an openable and closeable structure for capturing tissue between first and second tissue-engaging surfaces, which can comprise actuatable components such as one or more clamps, jaws, loops, snares and the like. The proximal handle end 104 of the probe can carry various actuator mechanisms known in the art for actuating components of the system 100, and/or one or more footswitches can be used for actuating components of the system.

As can be seen in FIG. 2, the system 100 further includes a source 120 of a flowable liquid treatment media 121 that communicates with a flow channel 124 extending through the probe body 102 to at least one outlet 125 in the working end 110. The outlet 125 can be singular or multiple and have any suitable dimension and orientation as will be described further below. The distal tip 130 of the probe can be sharp for penetrating tissue, or can be blunt-tipped or open-ended with outlet 125. Alternatively, the working end 110 can be configured in any of the various embodiments shown in FIGS. 6A-6M and described further below.

In one embodiment shown in FIG. 2, an RF energy source 140 is operatively connected to a thermal energy source or emitter (e.g., opposing polarity electrodes 144a, 144b) in interior chamber 145 in the proximal handle end 104 of the probe for converting the liquid treatment media 121 from a liquid phase media to a non-liquid vapor phase media 122 with a heat of vaporization in the range of 60° C. to 200° C., or 80° C. to 120° C. A vaporization system using Rf energy and opposing polarity electrodes is disclosed in co-pending U.S. patent application Ser. No. 11/329,381 which is incorporated herein by reference. Another embodiment of vapor generation system is described in below in the Section titled "INDUCTIVE VAPOR GENERATION SYSTEMS". In any system embodiment, for example in the system of FIG. 2, a controller 150 is provided that comprises a computer control system configured for controlling the operating parameters of inflows of liquid treatment media source 120 and energy applied to the liquid media by an energy source to cause the liquid-to-vapor conversion. The vapor generation systems described herein can consistently produce a high quality vapor having a temperature of at least 80° C., 100° C. 120° C., 140° C. and 160° C.

As can be seen in FIG. 2, the medical system 100 can further include a negative pressure or aspiration source indicated at 155 that is in fluid communication with a flow channel in probe 102 and working end 110 for aspirating treatment vapor media 122, body fluids, ablation by-products, tissue debris and the like from a targeted treatment site, as will be further described below. In FIG. 2, the controller 150 also is capable of modulating the operating parameters of the negative pressure source 155 to extract vapor media 122 from the treatment site or from the interior of the working end 110 by means of a recirculation channel to control flows of vapor media 122 as will be described further below.

In another embodiment, still referring to FIG. 2, medical system 100 further includes secondary media source 160 for providing an inflow of a second media, for example a biocompatible gas such as $CO_2$. In one method, a second media that includes at least one of depressurized $CO_2$, $N_2$, $O_2$ or $H_2O$ can be introduced and combined with the vapor media 122. This second media 162 is introduced into the flow of non-ionized vapor media for lowering the mass average temperature of the combined flow for treating tissue. In another embodiment, the medical system 100 includes a source 170 of a therapeutic or pharmacological agent or a sealant composition indicated at 172 for providing an additional treatment effect in the target tissue. In FIG. 2, the controller indicated at 150 also is configured to modulate the operating parameters of source 160 and 170 to control inflows of a secondary vapor 162 and therapeutic agents, sealants or other compositions indicated at 172.

In FIG. 2, it is further illustrated that a sensor system 175 is carried within the probe 102 for monitoring a parameter of the vapor media 122 to thereby provide a feedback signal FS to the controller 150 by means of feedback circuitry to thereby allow the controller to modulate the output or operating parameters of treatment media source 120, energy source 140, negative pressure source 155, secondary media source 160 and therapeutic agent source 170. The sensor system 175 is further described below, and in one embodiment comprises a flow sensor to determine flows or the lack of a vapor flow. In another embodiment, the sensor system 175 includes a temperature sensor. In another embodiment, sensor system 175 includes a pressure sensor. In another embodiment, the sensor system 175 includes a sensor arrangement for determining the quality of the vapor media, e.g., in terms or vapor saturation or the like. The sensor systems will be described in more detail below.

Figure 3:
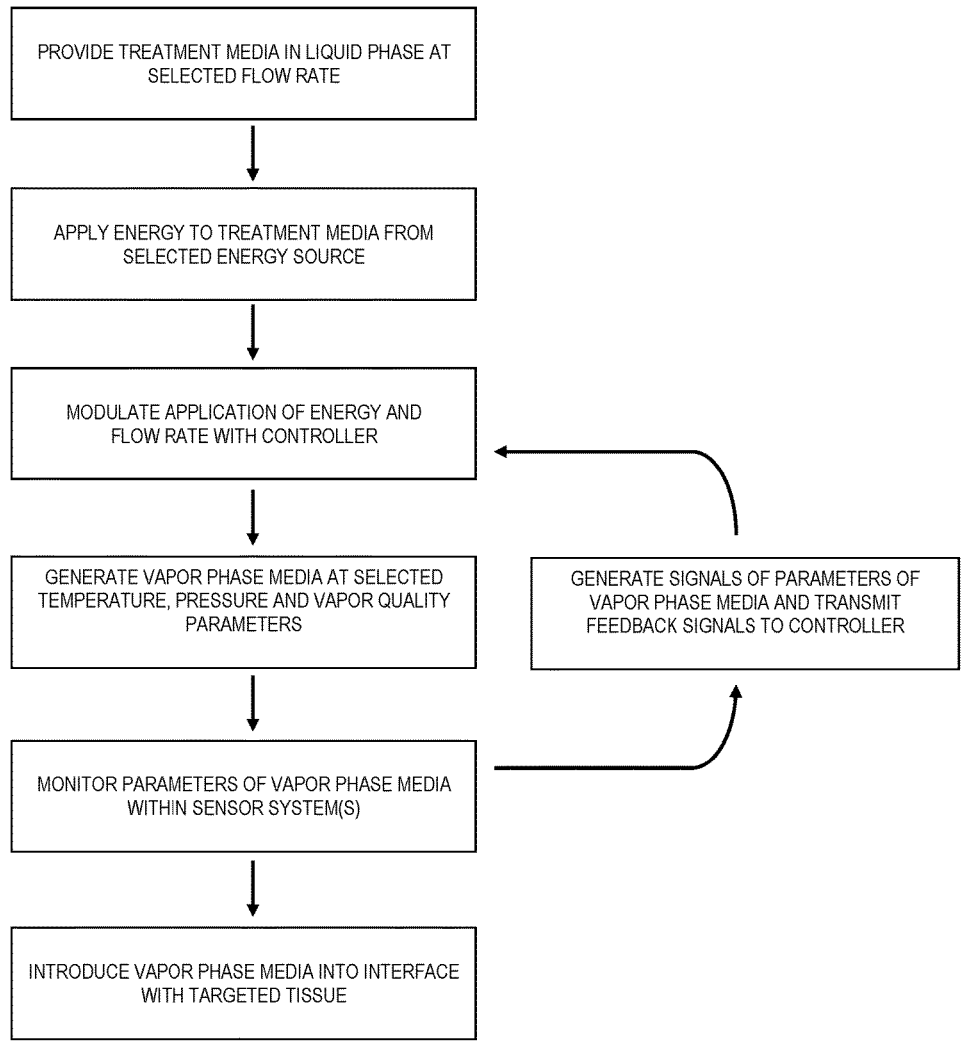
FIG. 3 is a block diagram of a control method of the invention.

Now turning to FIGS. 2 and 3, the controller 150 is capable of all operational parameters of system 100, including modulating the operational parameters in response to preset values or in response to feedback signals FS from sensor system(s) 175 within the system 100 and probe working end 110. In one embodiment, as depicted in the block diagram of FIG. 3, the system 100 and controller 150 are capable of providing or modulating an operational parameter comprising a flow rate of liquid phase treatment media 122 from pressurized source 120, wherein the flow rate is within a range from about 0.001 to 20 ml/min, 0.010 to 10 ml/min or 0.050 to 5 ml/min. The system 100 and controller 150 are further capable of providing or modulating another operational parameter comprising the inflow pressure of liquid phase treatment media 121 in a range from 0.5 to 1000 psi, 5 to 500 psi, or 25 to 200 psi. The system 100 and controller 150 are further capable of providing or modulating another operational parameter comprising a selected level of energy capable of converting the liquid phase media into a non-liquid, non-ionized gas phase media, wherein the energy level is within a range of about 5 to 2,500 watts; 10 to 1,000 watts or 25 to 500 watts. The system 100 and controller 150 are capable of applying the selected level of energy to provide the phase conversion in the treatment media over an interval ranging from 0.1 second to 10 minutes; 0.5 seconds to 5 minutes, and 1 second to 60 seconds. The system 100 and controller 150 are further capable of controlling parameters of the vapor phase media including the flow rate of non-ionized vapor media proximate an outlet 125, the pressure of vapor media 122 at the outlet, the temperature or mass average temperature of the vapor media, and the quality of vapor media as will be described further below.

Figure 4A:
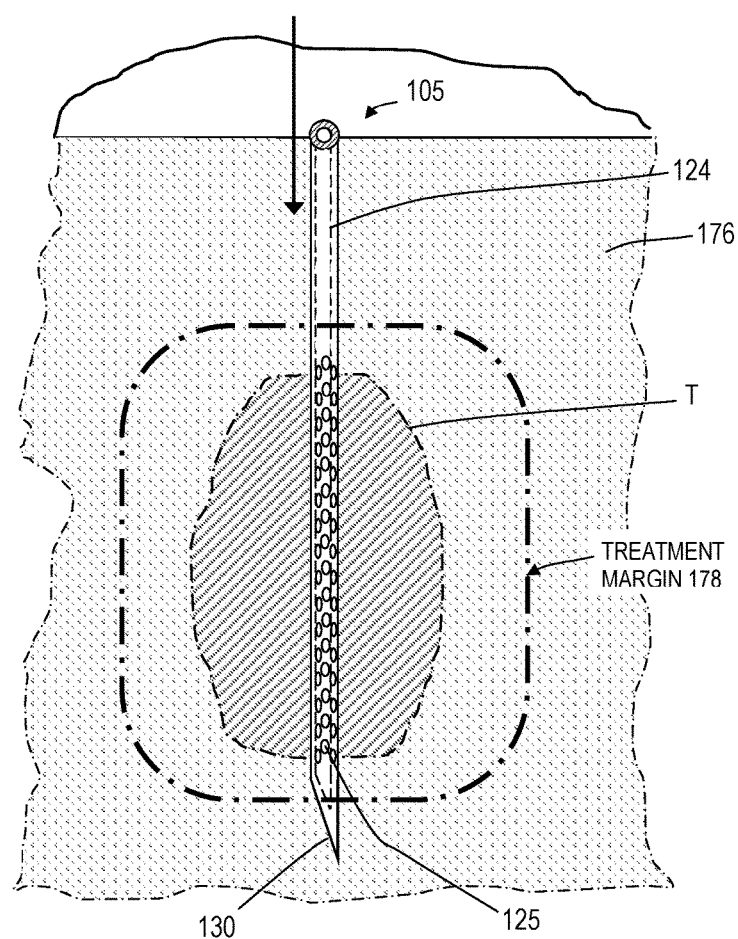
FIG. 4A is an illustration of the working end of FIG. 2 being introduced into soft tissue to treat a targeted tissue volume.
Figure 4B:
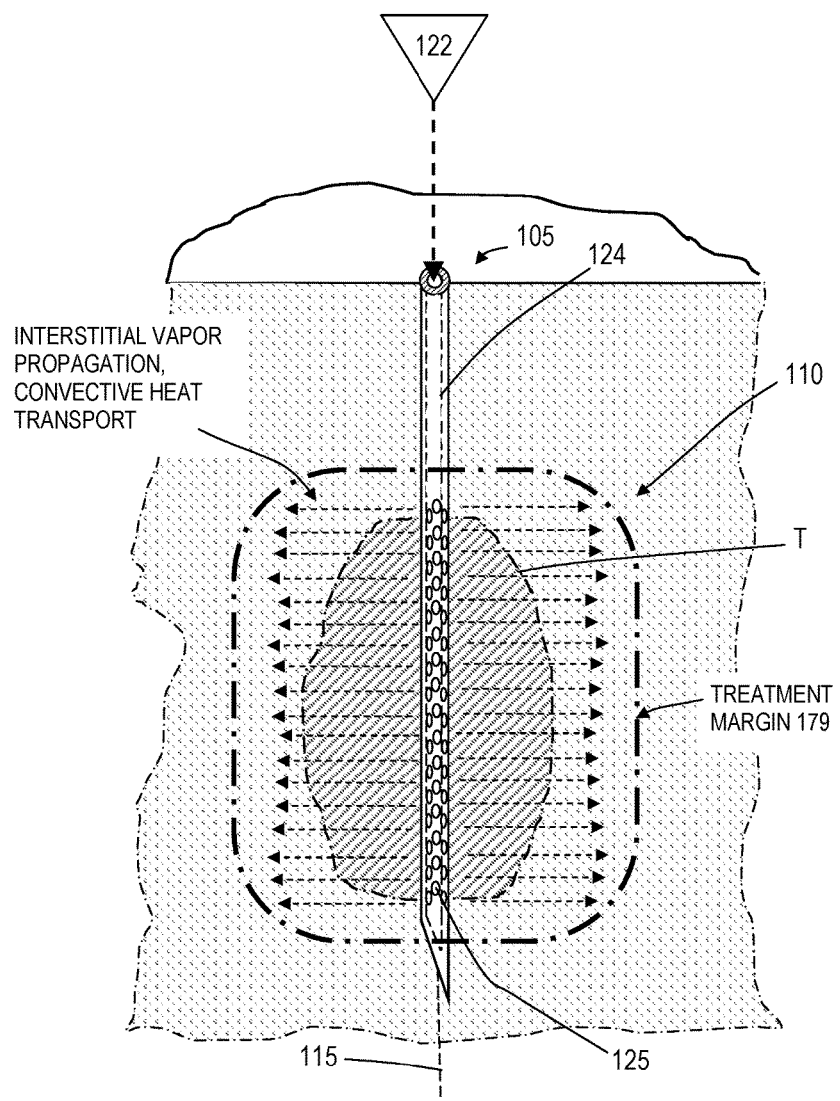
FIG. 4B is an illustration of the working end of FIG. 4A showing the propagation of vapor media in tissue in a method of use in ablating a tumor.

FIGS. 4A and 4B illustrate a working end 110 of the system 100 of FIG. 2 and a method of use. As can be seen in FIG. 4A, a working end 110 is singular and configured as a needle-like device for penetrating into and/or through a targeted tissue T such as a tumor in a tissue volume 176. The tumor can be benign, malignant, hyperplastic or hypertrophic tissue, for example, in a patient's breast, uterus, lung, liver, kidney, gall bladder, stomach, pancreas, colon, GI tract, bladder, prostate, bone, vertebra, eye, brain or other tissue. In one embodiment of the invention, the extension portion 104 is made of a metal, for example, stainless steel. Alternatively or additionally, at least some portions of the extension portion can be fabricated of a polymer material such as PEEK, PTFE, Nylon or polypropylene. Also optionally, one or more components of the extension portion are formed of coated metal, for example, a coating with Teflon® to reduce friction upon insertion and to prevent tissue sticking following use. In one embodiment at in FIG. 4A, the working end 110 includes a plurality of outlets 125 that allow vapor media to be ejected in all radial directions over a selected treatment length of the working end. In another embodiment, the plurality of outlets can be symmetric or asymmetric axially or angularly about the working end 110.

Figure 5:
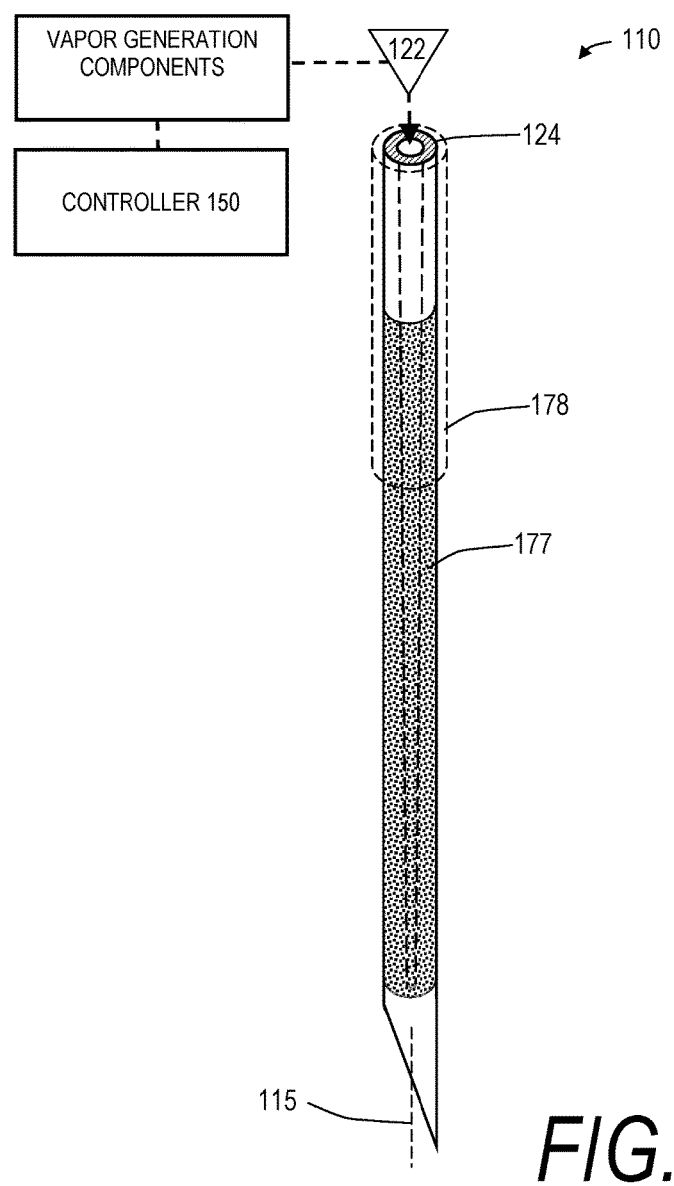
FIG. 5 is an illustration of a working end similar to FIGS. 4A-4B with vapor outlets comprising microporosities in a porous wall.

In one embodiment, the outer diameter of extension portion 105 or working end 110 is, for example, 0.2 mm, 0.5 mm, 1 mm, 2 mm, 5 mm or an intermediate, smaller or larger diameter. Optionally, the outlets can comprise microporosities 177 in a porous material as illustrated in FIG. 5 for diffusion and distribution of vapor media flows about the surface of the working end. In one such embodiment, such porosities provide a greater restriction to vapor media outflows than adjacent targeted tissue, which can vary greatly in vapor permeability. In this case, such microporosities insure that vapor media outflows will occur substantially uniformly over the surface of the working end. Optionally, the wall thickness of the working end 110 is from 0.05 to 0.5 mm. Optionally, the wall thickness decreases or increases towards the distal sharp tip 130 (FIG. 5). In one embodiment, the dimensions and orientations of outlets 125 are selected to diffuse and/or direct vapor media propagation into targeted tissue T and more particularly to direct vapor media into all targeted tissue to cause extracellular vapor propagation and thus convective heating of the target tissue as indicated in FIG. 4B. As shown in FIGS. 4A-4B, the shape of the outlets 125 can vary, for example, round, ellipsoid, rectangular, radially and/or axially symmetric or asymmetric. As shown in FIG. 5, a sleeve 178 can be advanced or retracted relative to the outlets 125 to provide a selected exposure of such outlets to provide vapor injection over a selected length of the working end 110. Optionally, the outlets can be oriented in various ways, for example so that vapor media 122 is ejected perpendicular to a surface of working end 110, or ejected is at an angle relative to the axis 115 or angled relative to a plane perpendicular to the axis. Optionally, the outlets can be disposed on a selected side or within a selected axial portion of working end, wherein rotation or axial movement of the working end will direct vapor propagation and energy delivery in a selected direction. In another embodiment, the working end 110 can be disposed in a secondary outer sleeve that has apertures in a particular side thereof for angular/axial movement in targeted tissue for directing vapor flows into the tissue.

FIG. 4B illustrates the working end 110 of system 100 ejecting vapor media from the working end under selected operating parameters, for example a selected pressure, vapor temperature, vapor quantity, vapor quality and duration of flow. The duration of flow can be a selected pre-set or the hyperechoic aspect of the vapor flow can be imaged by means of ultrasound to allow the termination of vapor flows by observation of the vapor plume relative to targeted tissue T. As depicted schematically in FIG. 4B, the vapor can propagate extracellularly in soft tissue to provide intense convective heating as the vapor collapses into water droplets which results in effective tissue ablation and cell death. As further depicted in FIG. 4B, the tissue is treated to provide an effective treatment margin 179 around a targeted tumorous volume. The vapor delivery step is continuous or can be repeated at a high repetition rate to cause a pulsed form of convective heating and thermal energy delivery to the targeted tissue. The repetition rate vapor flows can vary, for example with flow durations intervals from 0.01 to 20 seconds and intermediate off intervals from 0.01 to 5 seconds or intermediate, larger or smaller intervals.

In an exemplary embodiment as shown in FIGS. 4A-4B, the extension portion 105 can be a unitary member such as a needle. In another embodiment, the extension portion 105 or working end 110 can be a detachable flexible body or rigid body, for example of any type selected by a user with outlet sizes and orientations for a particular procedure with the working end attached by threads or Luer fitting to a more proximal portion of probe 102.

Figures 6A, 6B, 6C, 6D, 6E:
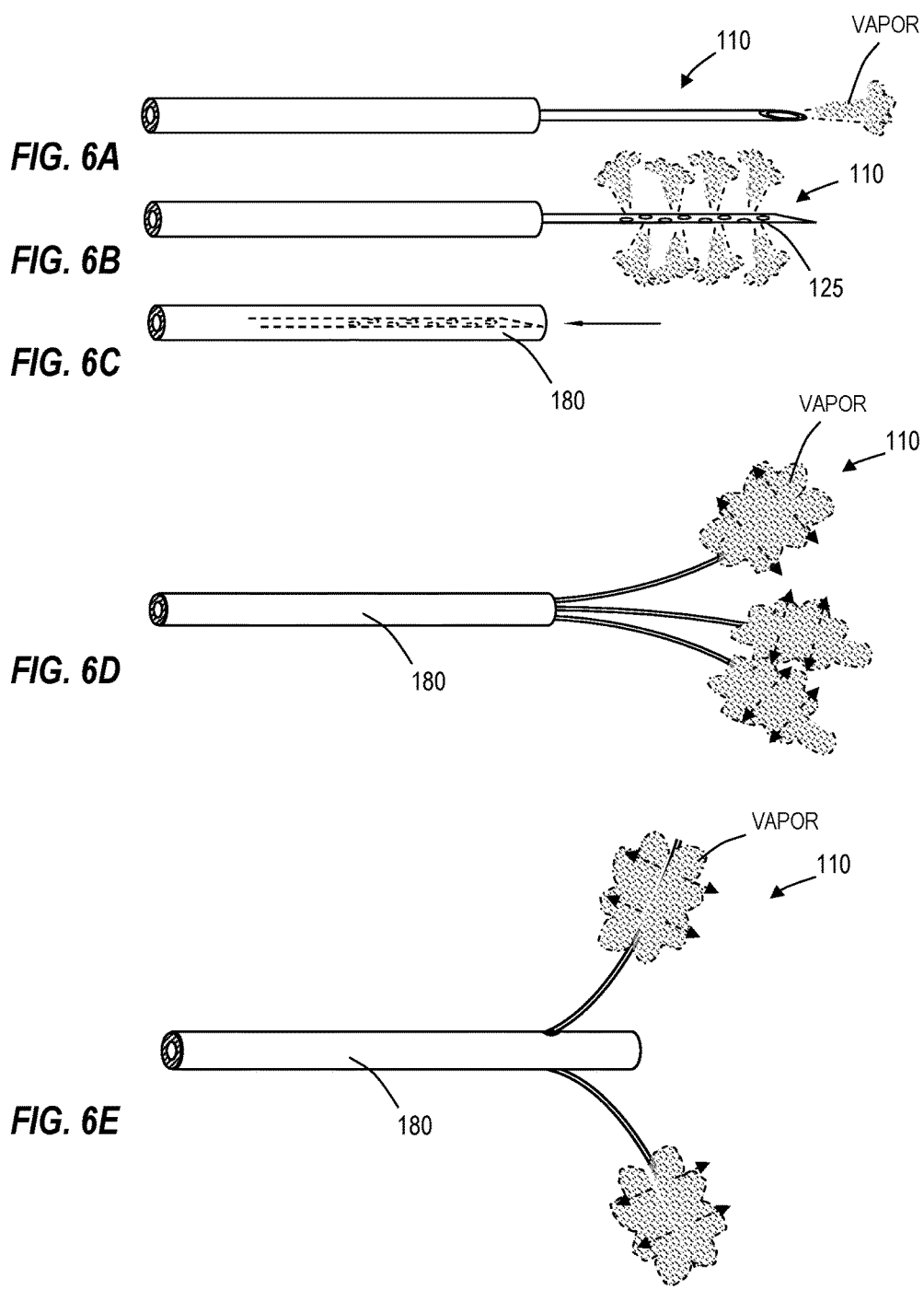
FIG. 6A is schematic view of a needle-type working end of a vapor delivery tool for applying energy to tissue.
FIG. 6B is schematic view of an alternative needle-type working end similar to FIG. 6A.
FIG. 6C is schematic view of a retractable needle-type working end similar to FIG. 6B.
FIG. 6D is schematic view of working end with multiple shape-memory needles.
FIG. 6E is schematic view of a working end with deflectable needles.
Figure 6F:
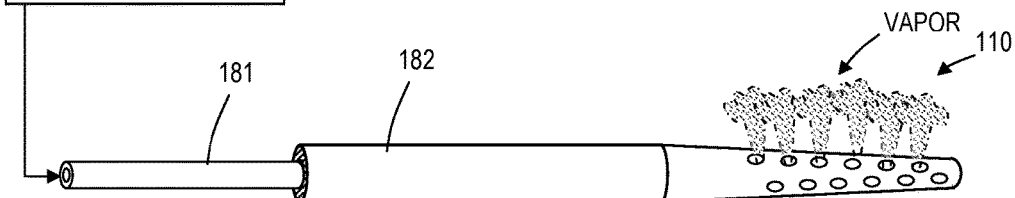
FIG. 6F is schematic view of a working end with a rotating element for directing vapor flows.
Figure 6G:
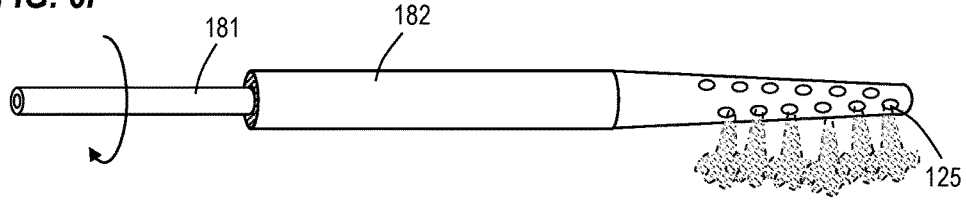
FIG. 6G is another view of the working end of FIG. 6F.

In other embodiments, the working end 110 can comprise needles with terminal outlets or side outlets as shown in FIGS. 6A-6B. The needle of FIGS. 6A and 6B can comprise a retractable needle as shown in FIG. 6C capable of retraction into probe or sheath 180 for navigation of the probe through a body passageway or for blocking a portion of the vapor outlets 125 to control the geometry of the vapor-tissue interface. In another embodiment shown in FIG. 6D, the working end 110 can have multiple retractable needles that are of a shape memory material. In another embodiment as depicted in FIG. 6E, the working end 110 can have at least one deflectable and retractable needle that deflects relative to an axis of the probe 180 when advanced from the probe. In another embodiment, the working end 110 as shown in FIGS. 6F-6G can comprise a dual sleeve assembly wherein vapor-carrying inner sleeve 181 rotates within outer sleeve 182 and wherein outlets in the inner sleeve 181 only register with outlets 125 in outer sleeve 182 at selected angles of relative rotation to allow vapor to exit the outlets. This assembly thus provides for a method of pulsed vapor application from outlets in the working end. The rotation can be from about 1 rpm to 1000 rpm.

Figure 6H:
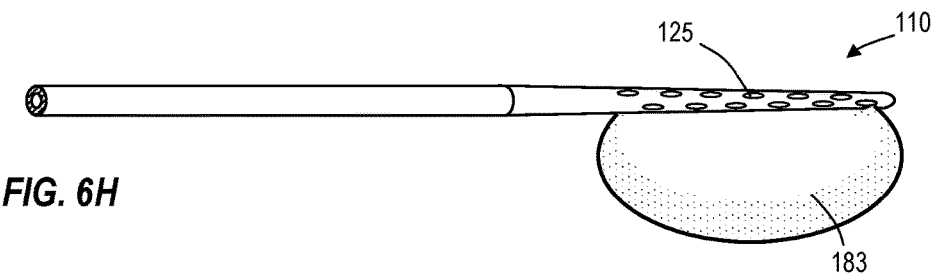
FIG. 6H is schematic view of a working end with a balloon.
Figure 6I:
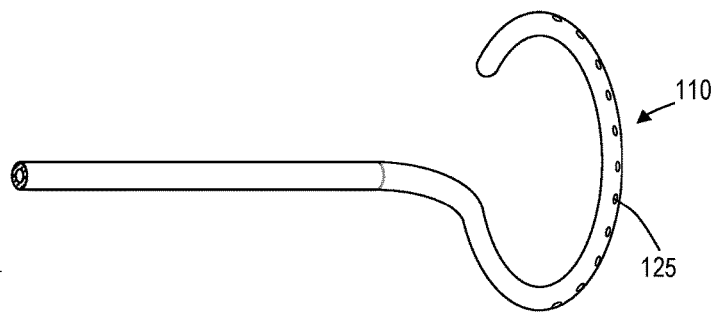
FIG. 6I is schematic view of an articulating working end.

In another embodiment of FIG. 6H, the working end 110 has a heat applicator surface with at least one vapor outlet 125 and at least one expandable member 183 such as a balloon for positioning the heat applicator surface against targeted tissue, In another embodiment of FIG. 6I, the working end can be a flexible material that is deflectable by a pull-wire as is known in the art. The embodiments of FIGS. 6H and 6I have configurations for use in treating atrial fibrillation, for example in pulmonary vein ablation.

Figure 6J:
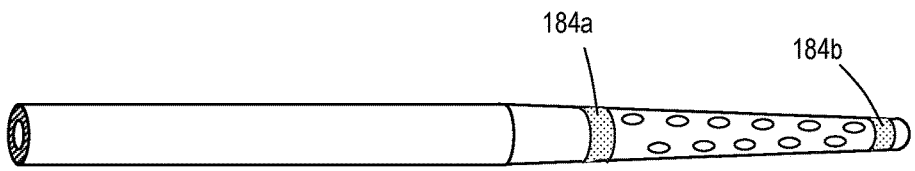
FIG. 6J is schematic view of an alternative working end with RF electrodes.
Figure 6K:
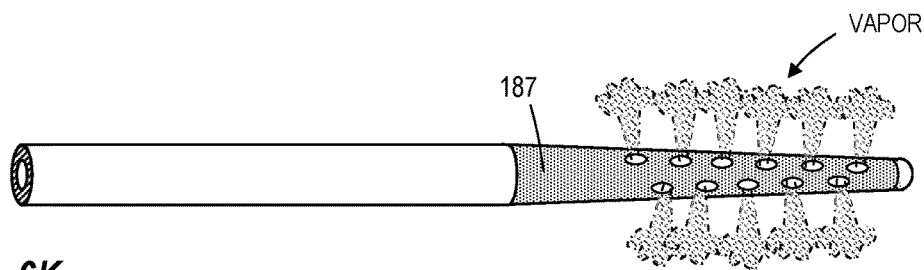
FIG. 6K is schematic view of an alternative working end with a resistive heating element.
Figure 6L:
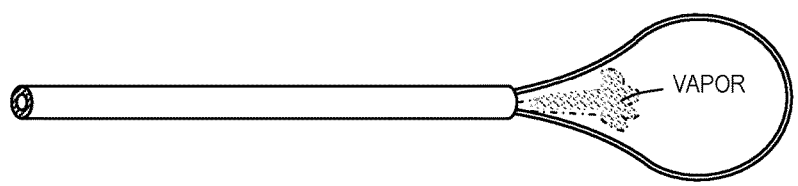
FIG. 6L is schematic view of a working end with a tissue-capturing loop.
Figure 6M:
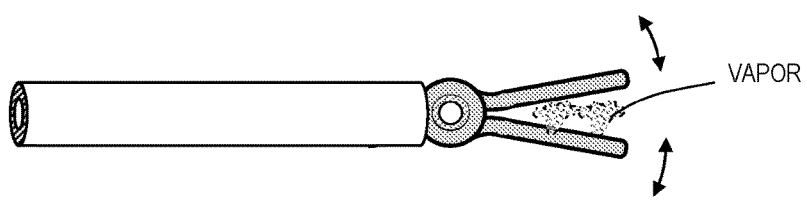
FIG. 6M is schematic view of an alternative working end with jaws for capturing and delivering vapor to tissue.

In another embodiment of FIG. 6J, the working end 110 includes additional optional heat applicator means which can comprise a mono-polar electrode cooperating with a ground pad or bi-polar electrodes 184a and 184b for applying energy to tissue. In FIG. 6K, the working end 110 includes resistive heating element 187 for applying energy to tissue. FIG. 6L depicts a snare for capturing tissue to be treated with vapor and FIG. 6M illustrates a clamp or jaw structure. The working end 110 of FIG. 6M includes means actuatable from the handle for operating the jaws.

Sensors for Vapor Flows, Temperature, Pressure, Quality

Figure 7:
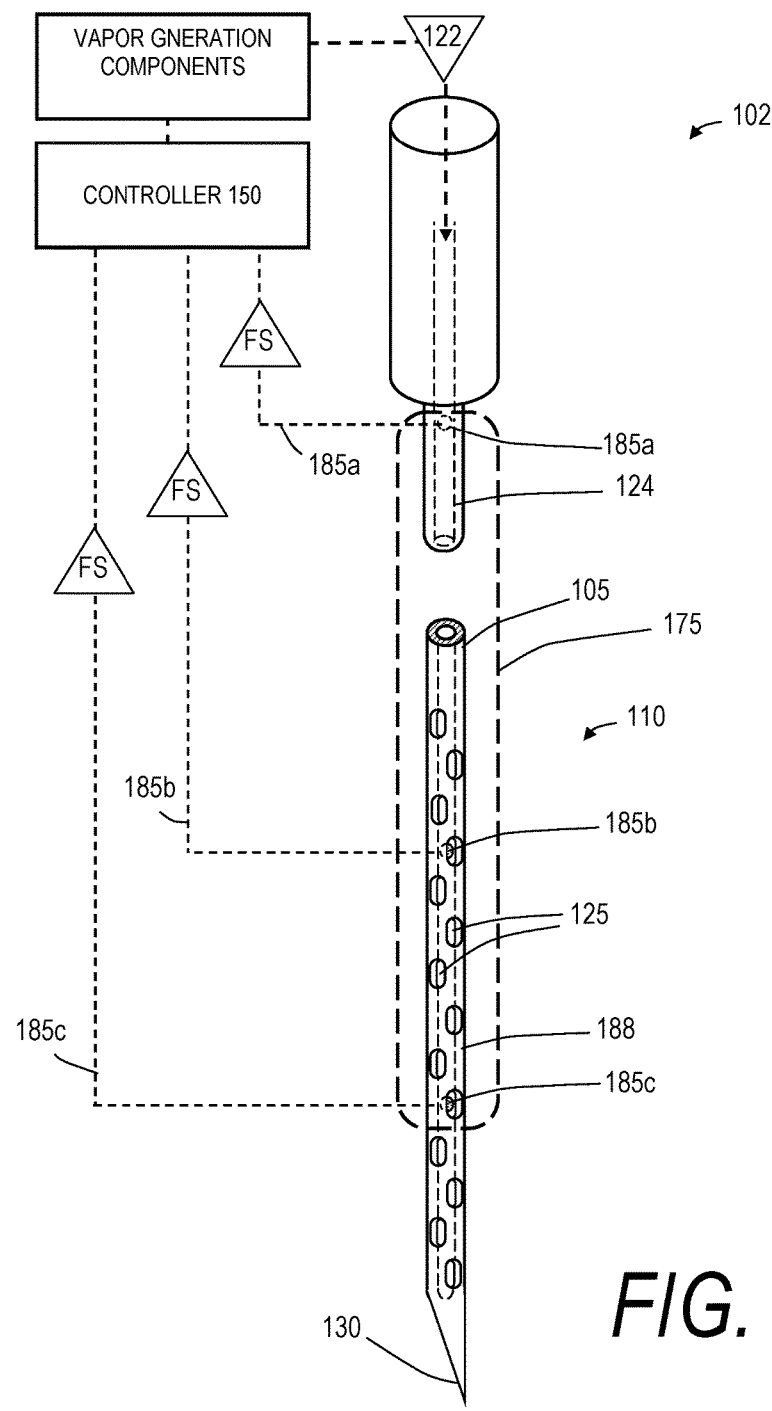
FIG. 7 illustrates an example of a sensor system for determining a vapor media flow parameter.

Referring to FIG. 7, one embodiment of sensor system 175 is shown that is carried by working end 110 of the probe 102 depicted in FIG. 2 for determining a first vapor media flow parameter, which can consist of determining whether the vapor flow is in an "on" or "off" operating mode. The working end 110 of FIG. 7 comprises a sharp-tipped needle suited for needle ablation of any neoplasia or tumor tissue, such as a benign or malignant tumor as described previously, but can also be any other form of vapor delivery tool. The needle can be any suitable gauge and in one embodiment has a plurality of vapor outlets 125. In a typical treatment of targeted tissue, it is important to provide a sensor and feedback signal indicating whether there is a flow, or leakage, of vapor media 122 following treatment or in advance of treatment when the system is in "off" mode. Similarly, it is important to provide a feedback signal indicating a flow of vapor media 122 when the system is in "on" mode. In the embodiment of FIG. 7, the sensor comprises at least one thermocouple or other temperature sensor indicated at 185a, 185b and 185c that are coupled to leads (indicated schematically at 186a, 186b and 186c) for sending feedback signals to controller 150. The temperature sensor can be a singular component or can be plurality of components spaced apart over any selected portion of the probe and working end. In one embodiment, a feedback signal of any selected temperature from any thermocouple in the range of the heat of vaporization of treatment media 122 would indicate that flow of vapor media, or the lack of such a signal would indicate the lack of a flow of vapor media. The sensors can be spaced apart by at least 0.05 mm, 1 mm, 5 mm, 10 mm and 50 mm. In other embodiments, multiple temperature sensing event can be averaged over time, averaged between spaced apart sensors, the rate of change of temperatures can be measured and the like. In one embodiment, the leads 186a, 186b and 186c are carried in an insulative layer of wall 188 of the extension member 105. The insulative layer of wall 188 can include any suitable polymer or ceramic for providing thermal insulation. In one embodiment, the exterior of the working end also is also provided with a lubricious material such as Teflon® which further insures against any tissue sticking to the working end 110.

Still referring to FIG. 7, a sensor system 175 can provide a different type of feedback signal FS to indicate a flow rate or vapor media based on a plurality of temperature sensors spaced apart within flow channel 124. In one embodiment, the controller 150 includes algorithms capable of receiving feedback signals FS from at least first and second thermocouples (e.g., 185a and 185c) at very high data acquisition speeds and compare the difference in temperatures at the spaced apart locations. The measured temperature difference, when further combined with the time interval following the initiation of vapor media flows, can be compared against a library to thereby indicate the flow rate.

Figure 8:
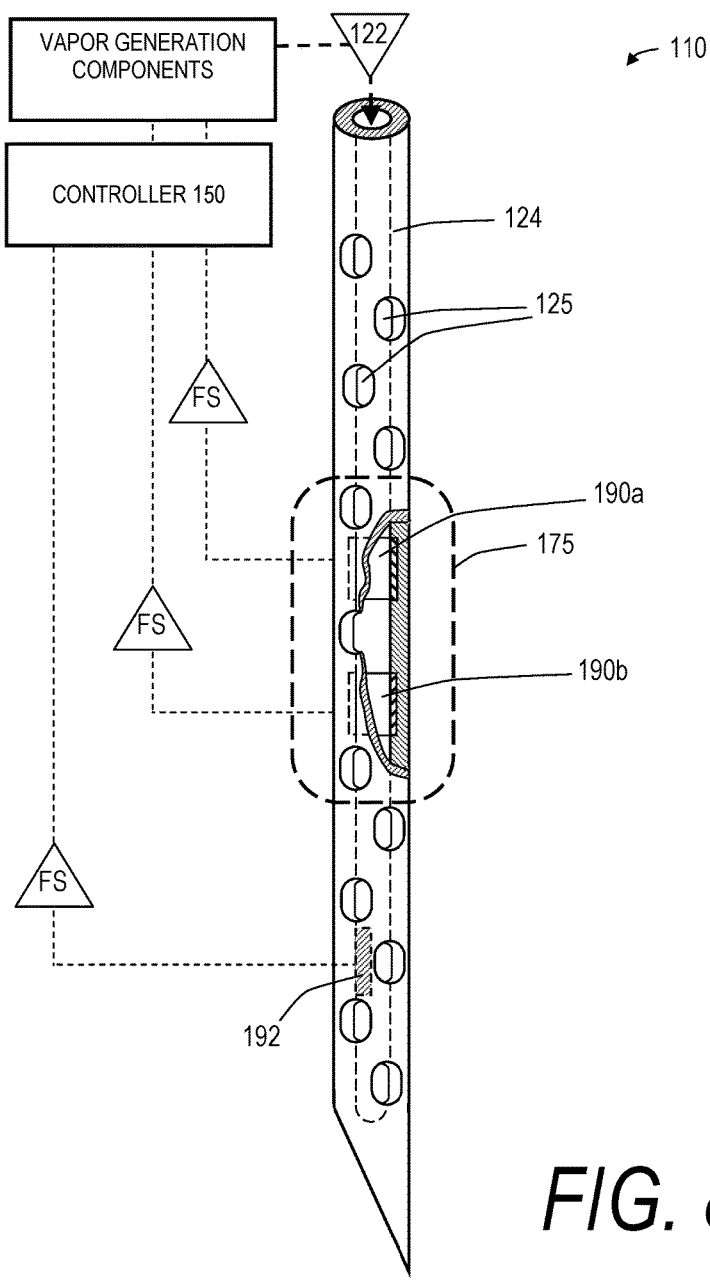
FIG. 8 illustrates an example of a sensor system for indicating vapor quality of the flow media.

Another embodiment of sensor system 175 in a similar working end 110 is depicted in FIG. 8, wherein the sensor is configured for indicating vapor quality—in this case based on a plurality of spaced apart electrodes 190a and 190b coupled to controller 150 and an electrical source (not shown). In this embodiment, a current flow is provided within a circuit to the spaced apart electrodes 190a and 190b and during vapor flows within channel 124 the impedance will vary depending on the vapor quality or saturation, which can be processed by algorithms in controller 150 and can be compared to a library of impedance levels, flow rates and the like to thereby determine vapor quality. It is important to have a sensor to provide feedback of vapor quality, which determines how much energy is being carried by a vapor flow. The term "vapor quality" is herein used to describe the percentage of the flow that is actually water vapor as opposed to water droplets that is not phase-changed. In another embodiment (not shown) an optical sensor can be used to determine vapor quality wherein a light emitter and receiver can determine vapor quality based on transmissibility or reflectance of a vapor flow.

Figure 1A:
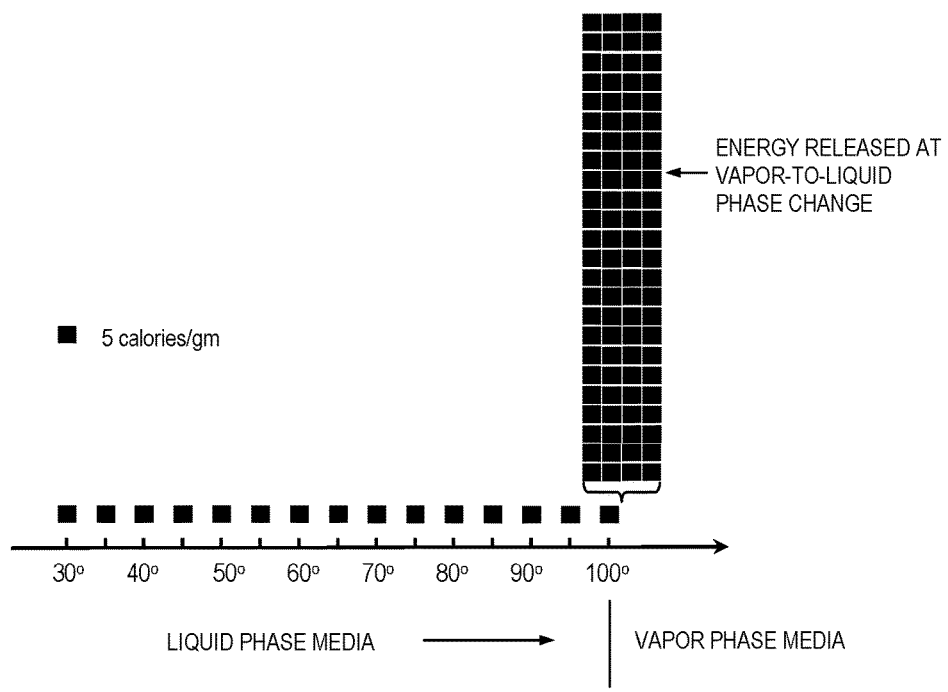
FIG. 1A is a graphical depiction of the quantity of energy needed to achieve the heat of vaporization of water.
Figure 1B:
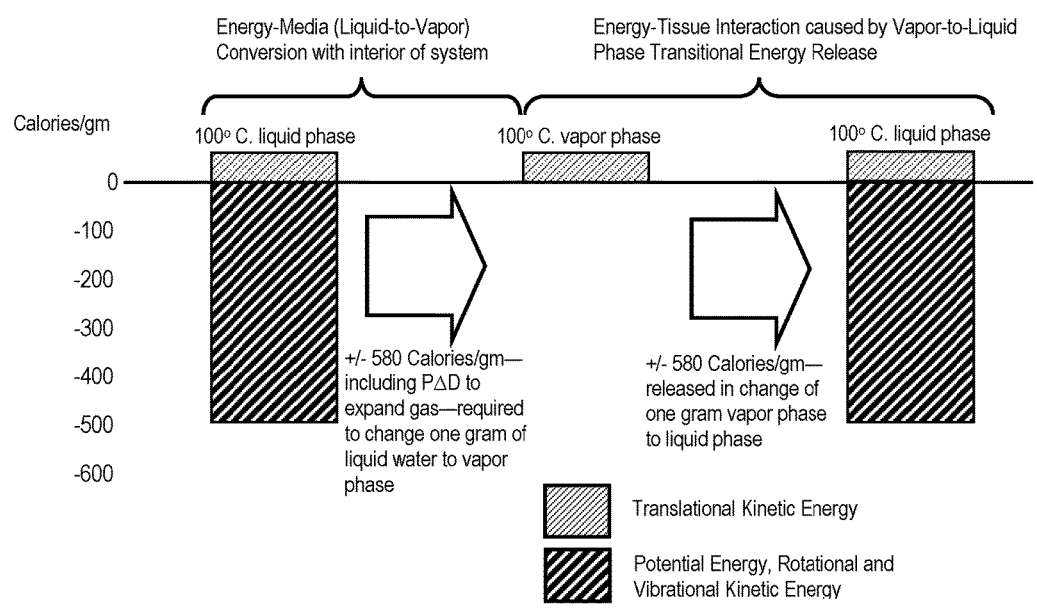
FIG. 1B is a diagram of phase change energy release that underlies a system and method of the invention.

FIG. 8 further depicts a pressure sensor 192 in the working end 110 for providing a signal as to vapor pressure. In operation, the controller can receive the feedback signals FS relating to temperature, pressure and vapor quality to thereby modulate all other operating parameters described above to optimize flow parameters for a particular treatment of a target tissue, as depicted in FIG. 1. In one embodiment, a MEMS pressure transducer is used, which are known in the art. In another embodiment, a MEMS accelerometer coupled to a slightly translatable coating can be utilized to generate a signal of changes in flow rate, or a MEMS microphone can be used to compare against a library of acoustic vibrations to generate a signal of flow rates.

Figure 9A:
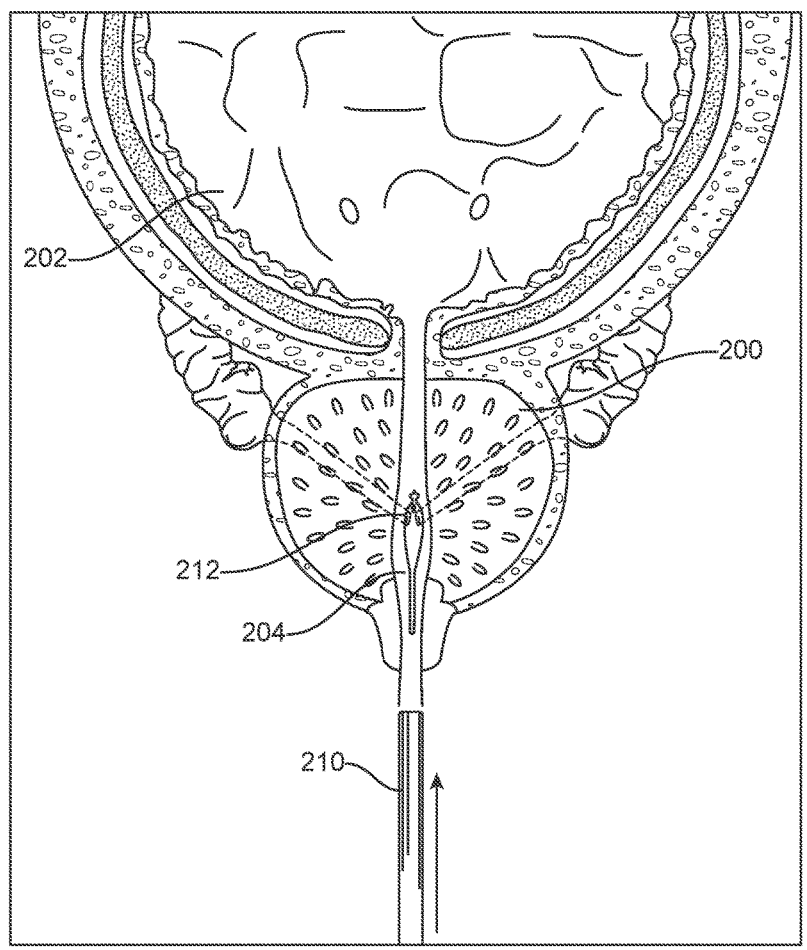
FIG. 9A is an illustration of a method of using a vapor delivery tool for treating prostate tissue.
Figure 9B:
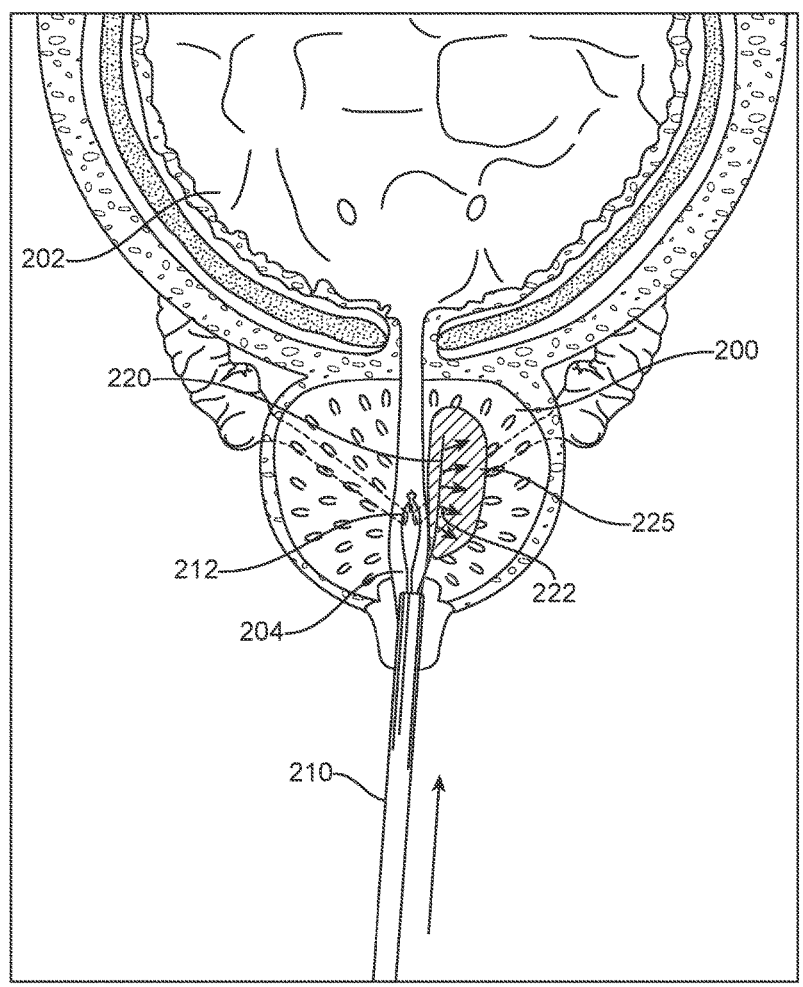
FIG. 9B is an illustration of the method and vapor delivery tool of FIG. 9A showing the propagation of vapor to treat prostate tissue.

FIGS. 9A and 9B depict another system, vapor delivery tool and method of use configured for treating a prostate disorder such as BPH, prostatitis or prostate cancer. FIG. 9A depicts a patients prostate 200, bladder 202 and urethra 204 wherein BPH causes a restriction on the urethra. As can be seen in FIGS. 9A and 9B, a rigid or flexible endoscope 210 is introduced trans-urethrally into the prostate 200. In FIG. 9B, a landmark such as the verumontanum 212 is identified. The scope can then be angled, articulated and retracted if desired to then introduce the working end 220 of an elongated vapor tool or needle into the prostate tissue. As can be seen in FIG. 9B, vapor media 222 is injected into the prostate tissue to ablate a tissue volume 225 as generally described in the text related to FIGS. 2-5, which allows for ablation of prostate tissue. The treated tissue will then reabsorb and reduce the prostatic volume, which in turn will reduce the restriction on the urethra 204. In general, a method of treating BPH prostatitus or prostate cancer comprising introducing a gas interstitially in prostate tissue wherein the gas provides localized or global ablation of prostate tissue within the prostate capsule. In FIG. 9B, it can be understood that the treatment would be repeated in each prostate lobe. As described above in other embodiments, the method of treating prostate tissue in this case comprise causing a controlled vapor-to-liquid phase state change of a selected gas or vapor media in prostate tissue thereby applying energy substantially equal to the heat of vaporization to elevate the temperature of said prostate tissue to cause a therapeutic effect.

In one method of the invention, a system is provided including an elongated probe with a terminal portion positioned within a prostate, followed by the step of injecting a selected media from the terminal portion into the prostate, and then causing a controlled vapor-to-liquid phase state change of the selected media thereby applying energy substantially equal to the heat of vaporization to elevate the temperature of said prostate tissue to cause a therapeutic effect therein. The method of ablating tissue optionally includes controlling an operational parameter such as (i) controlling the temperature of the vapor-to-liquid phase state change of the vapor media, (ii) controlling the pressure of the vapor flow, (iii) controlling the volume of the vapor flow, and (iv) controlling the rate of delivery of vapor flow. In general, this method of treating tissue to cause a therapeutic effect includes applying energy from a thermal energy emitter to tissue to cause cell death in the tissue, wherein the applied energy causes cell death without carbonization potential. This effect is important as the inflammatory response is reduced substantially. Of particular interests, the method of ablating tissue allows for greatly reduced applied energy, wherein the controlled flow of a vapor media from a probe into tissue is provided at a sufficient rate to propagate within extracellular spaces to ablate the tissue. In this method, the vapor media applies substantial ablative energy to cell lipid bilayers or membranes by release of energy from a vapor-to-liquid phase state change, wherein vapor media applies non-substantial ablative energy to the interior of cells thereby to thereby reduce applied energy. In other words, the fluid content of cells does not need to be ablated to cause cell death—which is the manner of operation of other ablative energy modalities such as RF, laser, microwave, ultrasound and the like.

Inductive Vapor Generation Systems

Figure 10:
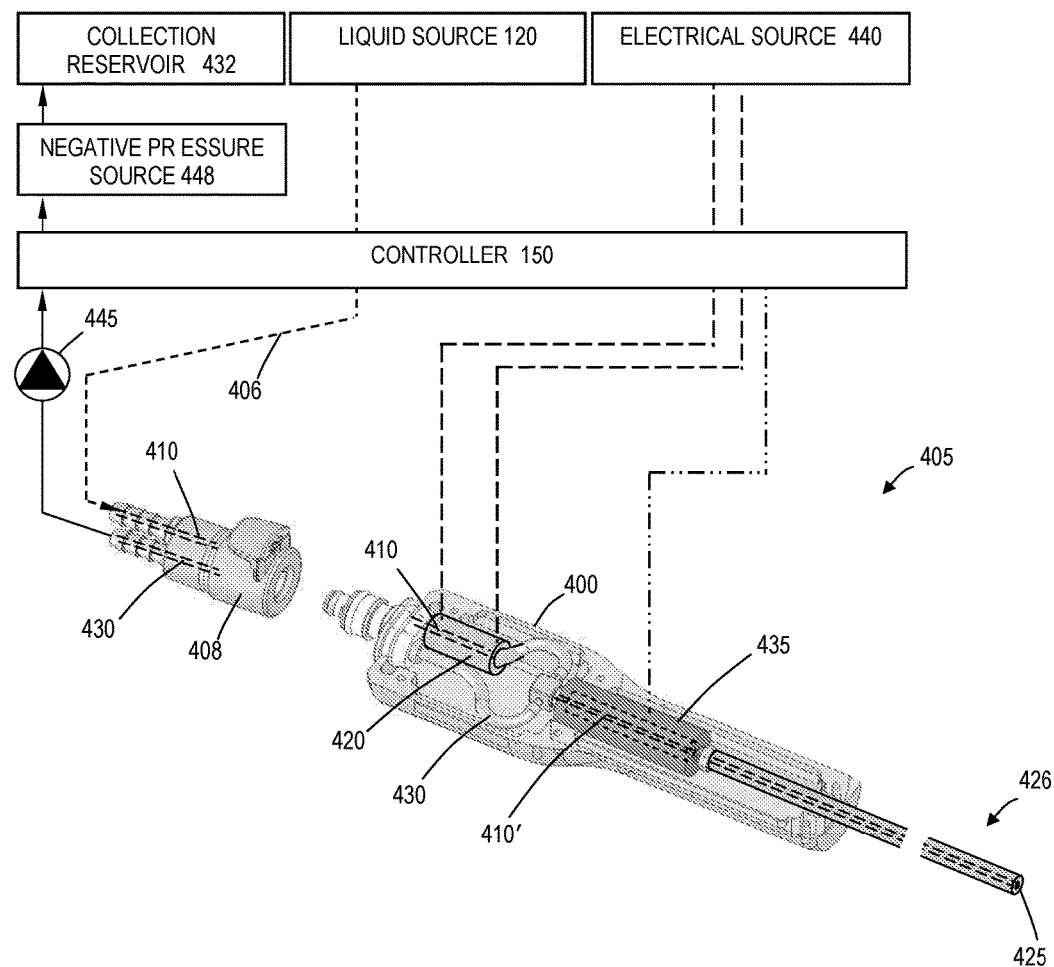
FIG. 10 is a partly disassembled view of a handle and inductive vapor generator system of the invention.
Figure 11:
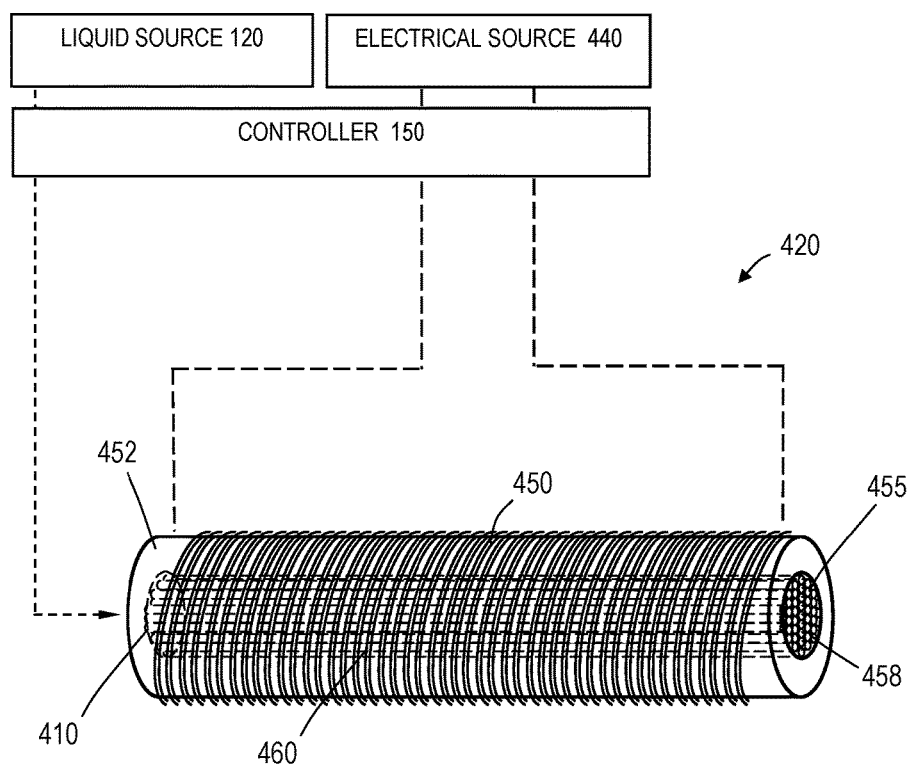
FIG. 11 is an enlarged schematic view of the inductive vapor generator of FIG. 10.

FIGS. 10 and 11 depict a vapor generation component that utilizes and an inductive heating system within a handle portion 400 of the probe or vapor delivery tool 405. In FIG. 10, it can be seen that a pressurized source of liquid media 120 (e.g., water or saline) is coupled by conduit 406 to a quick-connect fitting 408 to deliver liquid into a flow channel 410 extending through an inductive heater 420 in probe handle 400 to at least one outlet 425 in the working end 426. In one embodiment shown in FIG. 10, the flow channel 410 has a bypass or recirculation channel portion 430 in the handle or working end 426 that can direct vapor flows to a collection reservoir 432. In operation, a valve 435 in the flow channel 410 thus can direct vapor generated by inductive heater 420 to either flow channel portion 410' or the recirculation channel portion 430. In the embodiment of FIG. 10, the recirculation channel portion 430 also is a part of the quick-connect fitting 408.

In FIG. 10, it can be seen that the system includes a computer controller 150 that controls (i) the electromagnetic energy source 440 coupled to inductive heater 420, (ii) the valve 435 which can be an electrically-operated solenoid, (iii) an optional valve 445 in the recirculation channel 430 that can operate in unison with valve 435, and (iv) optional negative pressure source 448 operatively coupled to the e recirculation channel 430.

In general, the system of the invention provides a small handheld device including an assembly that utilized electromagnetic induction to turn a sterile water flow into superheated or dry vapor which can be propagated from at least one outlet in a vapor delivery tool to interface with tissue and thus ablate tissue. In one aspect of the invention, an electrically-conducting microchannel structure or other flow-permeable structure is provided and an inductive coil causes electric current flows in the structure. Eddies within the current create magnetic fields, and the magnetic fields oppose the change of the main field thus raising electrical resistance and resulting in instant heating of the microchannel or other flow-permeable structure. In another aspect of the invention, it has been found that corrosion-resistant microtubes of low magnetic 316 SS are best suited for the application, or a sintered microchannel structure of similar material. While magnetic materials can improve the induction heating of a metal because of ferromagnetic hysteresis, such magnetic materials (e.g. carbon steel) are susceptible to corrosion and are not optimal for generating vapor used to ablate tissue. In certain embodiments, the electromagnetic energy source 440 is adapted for inductive heating of a microchannel structure with a frequency in the range of 50 kHz to 2 Mhz, and more preferably in the range of 400 kHz to 500 kHz. While a microchannel structure is described in more detail below, it should be appreciated that the scope of the invention includes flow-permeable conductive structures selected from the group of woven filaments structures, braided filament structures, knit filaments structures, metal wool structures, porous structures, honeycomb structure and an open cell structures.

In general, a method of the invention comprises utilizing an inductive heater 420 of FIGS. 10-11 to instantly vaporize a treatment media such as deionized water that is injected into the heater at a flow rate of ranging from 0.001 to 20 ml/min, 0.010 to 10 ml/min, 0.050 to 5 ml/min., and to eject the resulting vapor into body structure to ablate tissue. The method further comprises providing an inductive heater 420 configured for a disposable hand-held device (see FIG. 10) that is capable of generating a minimum water vapor that is at least 70% water vapor, 80% water vapor and 90% water vapor.

FIG. 11 is an enlarged schematic view of inductive heater 420 which includes at least one winding of inductive coil 450 wound about an insulative sleeve 452. The coil 450 is typically wound about a rigid insulative member, but also can comprise a plurality of rigid coil portions about a flexible insulator or a flexible coil about a flexible insulative sleeve. The coil can be in handle portion of a probe or in a working end of a probe such as a catheter. The inductive coil can extends in length at least 5 mm, 10 mm, 25 mm, 50 mm or 100 m.

In one embodiment shown schematically in FIG. 11, the inductive heater 420 has a flow channel 410 in the center of insulative sleeve 452 wherein the flows passes through an inductively heatable microchannel structure indicated at 455. The microchannel structure 455 comprises an assembly of metal hypotubes 458, for example consisting of thin-wall biocompatible stainless steel tube tightly packed in bore 460 of the assembly. The coil 450 can thereby inductively heat the metal walls of the microchannel structure 455 and the very large surface area of structure 455 in contact with the flow can instantly vaporize the flowable media pushed into the flow channel 410. In one embodiment, a ceramic insulative sleeve 452 has a length of 1.5" and outer diameter of 0.25" with a 0.104" diameter bore 460 therein. A total of thirty-two 316 stainless steel tubes 458 with 0.016" O.D., 0.010" I.D., and 0.003" wall are disposed in bore 460. The coil 450 has a length of 1.0" and comprises a single winding of 0.026" diameter tin-coated copper strand wire (optionally with ceramic or Tefloe insulation) and can be wound in a machined helical groove in the insulative sleeve 452. A 200

W RF power source 440 is used operating at 400 kHz with a pure sine wave. A pressurized sterile water source 120 comprises a computer controlled syringe that provides fluid flows of deionized water at a rate of 3 ml/min which can be instantly vaporized by the inductive heater 420. At the vapor exit outlet or outlets 125 in a working end, it has been found that various pressures are needed for various tissues and body cavities for optimal ablations, ranging from about 0.5 to 20 psi for ablating body cavities or lumens and about 10 psi to 200 psi for interstitial ablations.

Figure 12:
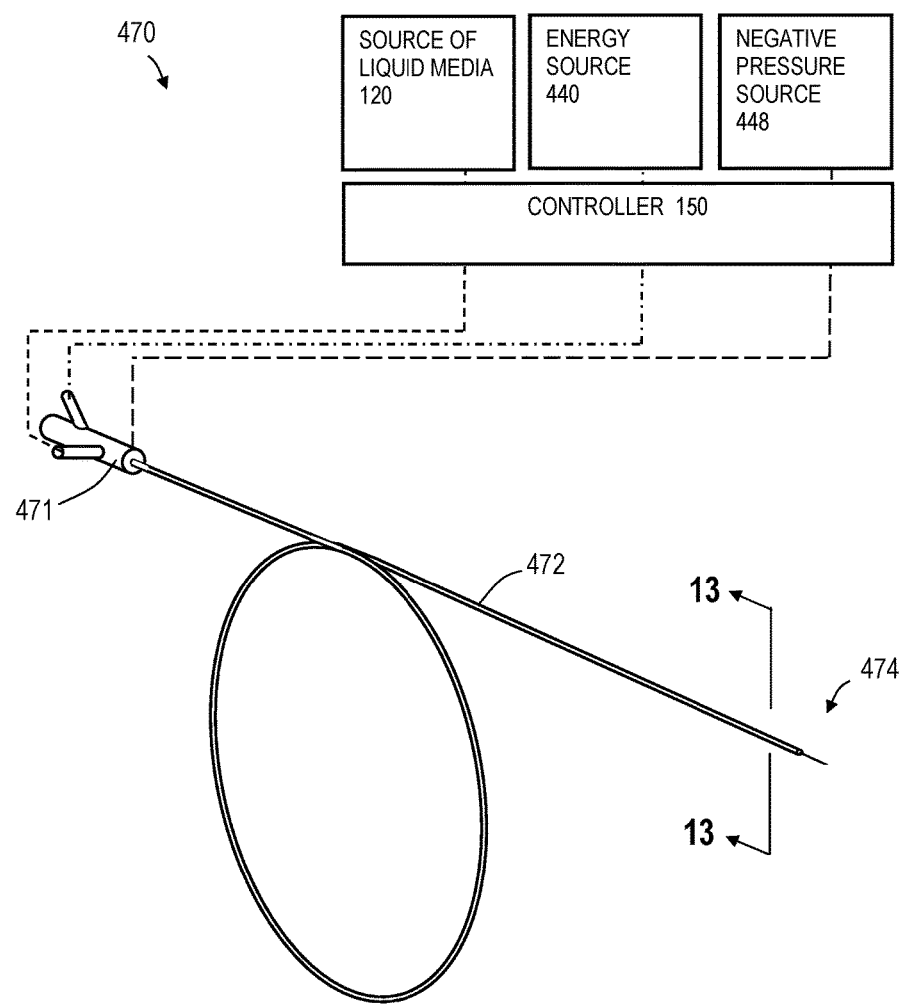
FIG. 12 is a perspective schematic view of another vapor delivery tool with an inductive vapor generator in a flexible probe member.

FIG. 12 illustrates a portion of an alternative vapor delivery tool 470 that comprises a handle portion 471 coupled to an elongated member 472 having an inductive coil 450 similar to that of FIG. 11. The working end 474 can include an extendable needle as depicted in FIG. 12 or can comprise other working end as depicted in FIGS. 6A-6M. In one embodiment shown in FIGS. 12 and 13, the coil 450 is disposed about a flexible inner sleeve 476 fabricated of a suitable heat resistant plastic such as PEEK or a polyether block amide known in the art. The coil and inner sleeve assembly is surrounded by an outer flexible thermally insulative sleeve 477. The inductively heatable structure 480 can be a 316 SS hypotube that is cut into a helical form for flexibility with flow channel 410 extending therethrough. In all other respects, the inductive heater 420 of FIG. 12 functions as described previously.

Figure 13:
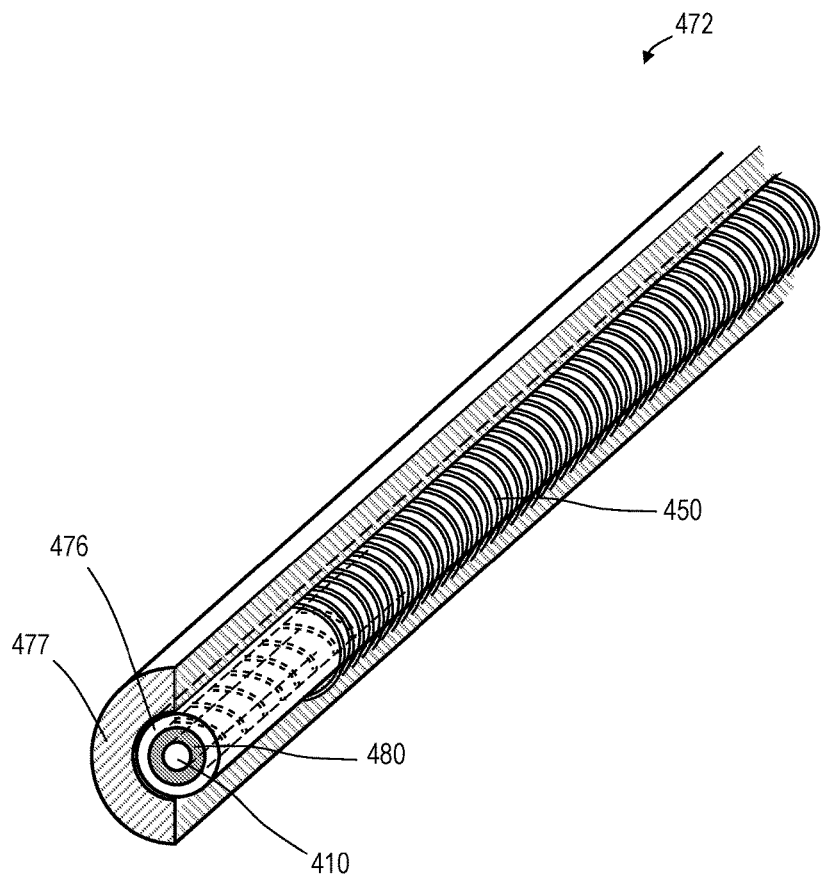
FIG. 13 is a cut-away view of the inductive vapor generator of FIG. 12.
Figure 14:
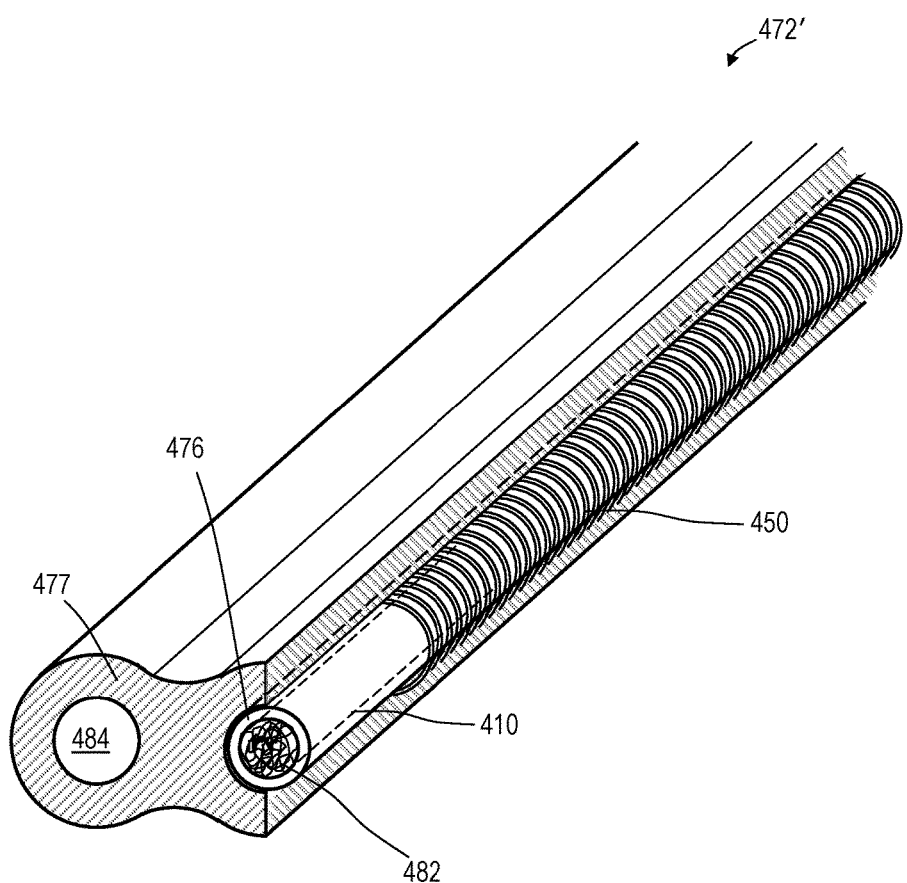
FIG. 14 is a cut-away view of an alternative inductive vapor generator similar to that of FIG. 13.

FIG. 14 illustrates another elongated member 472' that is similar to that of FIG. 13 except for the coil 450 is disposed about an insulative inner sleeve 476 that carries an inductively heatable flow-permeable stainless steel wool 482 in flow channel 410. Further, the embodiment of FIG. 14 has a recirculation channel 484 for a looped flow of vapor as described above in the text referring to the system of FIG. 10.

Figure 15:
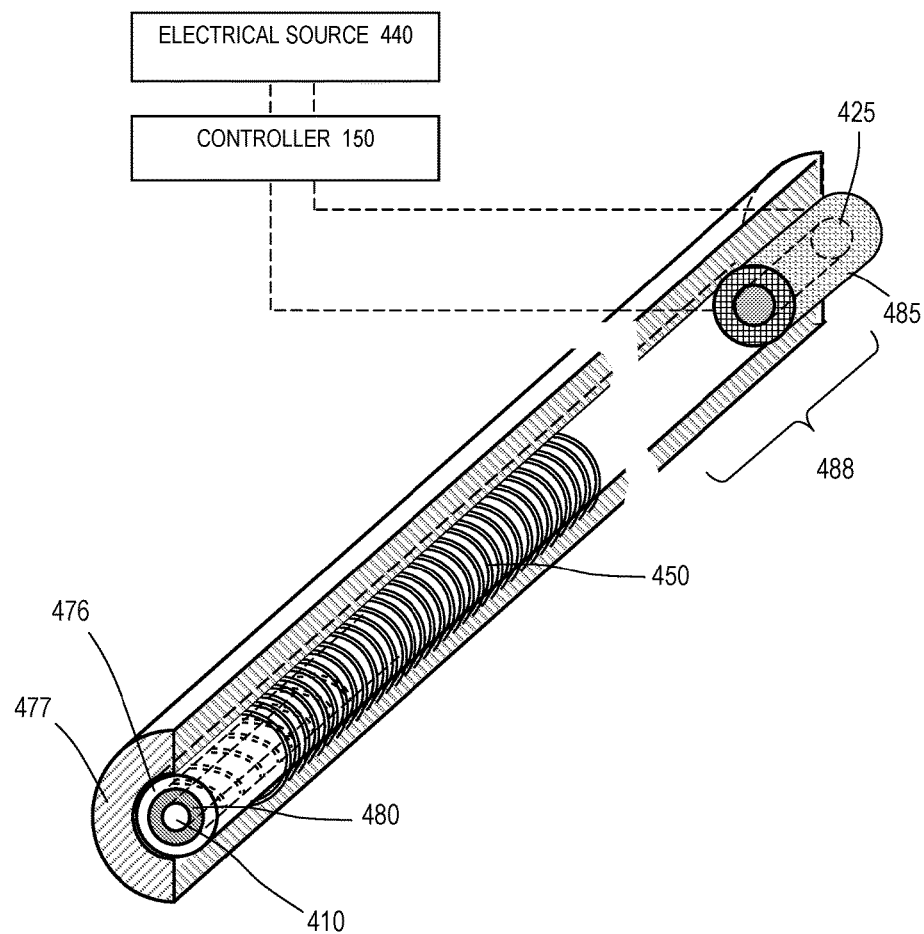
FIG. 15 is a cut-away view of an alternative vapor generator system with first and second heating systems.

FIG. 15 schematically depicts another embodiment similar to that of FIGS. 10-14 that includes an inductive coil 450 that is utilized to generate vapor in a first location in a probe. A second heating system indicated is provided at the working end 488 of the vapor delivery tool that comprises a microporous resistive heating element 485 proximate at least one vapor outlet 425. It has been found that such a microporous resistive heater can scrub any water droplets from the flow to provide very high quality vapor, for example a vapor that is at least 90% water vapor or at least 95% water vapor. The microporous resistive heating element 485 can comprise a sintered metal filter material with a mean pore dimension of less than 100 microns, less than 50 microns or less than 20 microns. The first heating element can be spaced apart from the second heating element by at least 50 mm. In one embodiment, the microporous material 485 is a resistively heatable nichrome that is coupled to electrical source 440 and controller 150 by opposing polarity electrical leads 490a and 490b to heat the material. The controller 150 can be configured to heat the microporous material 485 in conjunction with actuation of the fluid source and first proximal heater system.

Figure 16:
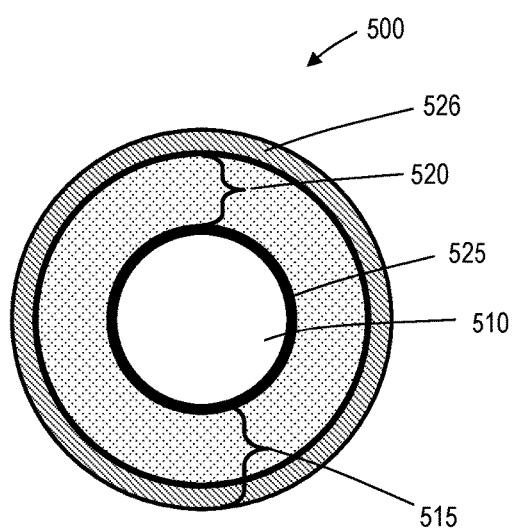
FIG. 16 is a sectional view of a vapor-deliver member showing thermally insulative layers.

In another aspect of the invention, a vapor delivery system as described above can have a rigid or flexible extension member 500 with an insulative wall, as depicted in the cross-sectional view of FIG. 16. In FIG. 16, it can be seen that at least one flow channel 510 is within an interior of the surrounding structure or wall 515 that includes a thermally insulative layer or region indicated at 520. In one embodiment, the extension member 500 has a thin inner layer 525 around the flow channel 510 which is of a biocompatible fluid impermeable material such as a polymer (Teflon®) or a metal such as a stainless steel. A flexible vapor delivery extension member can include an electroless plating over a polymer base to provide biocompatible inner layer 525. Outward from the inner layer 525 is the insulating region or layer 520 that can comprise air channels, voids with a partial vacuum, a region that carries an aerogel or aerogel particles optionally under a partial vacuum, a region that carries hollow glass or ceramic microspheres, or a region with a channel or multiple channels that provide for a flow of air or a liquid about the at least one flow channel 510. An extension member 500 that includes flow channels or recirculation channels can be coupled to any positive and negative pressure sources known in the art to cause a flow of air, cooling fluids, cryogenic fluids and the like through such channels. The exterior 526 of the wall 515 can be any suitable layer of a high temperature resistant polymer such as PEEK. Other materials used in an extension member can comprise formulations or blends of polymers that include, but are not limited to PTFE, polyethylene terephthalate (PET), or PEBAX. PTFE (polytetrafluoroethylene) is a fluoropolymer which has high thermal stability (up to 260° C.), is chemically inert, has a very low dielectric constant, a very low surface friction and is inherently flame retardant. A range of homo and co-fluoropolymers are commercialized under such names as Teflon®, Tefzel®, Neoflon®, Polyflon® and Hyflon®. In one embodiment, the insulative layer 520, or inner layer 525 and insulating layer 520 in combination, or the entire wall 515, can have a thermal conductivity of less than 0.05 W/mK, less than 0.01 W/mK or less than 0.005 W/mK. In another aspect of the invention, the wall is configured at least partially with materials interfacing the channel that have a heat capacity of less than 2000 J/kgK for reducing condensation in the flow channel upon the initiation of vapor flow therethrough.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method for thermally treating tissue comprising:
   providing a probe body having a flow channel extending therein to an outlet in a working end;
   introducing a flow of a liquid media through the flow channel;
   applying energy to the tissue by inductively heating a portion of the probe body sufficient to vaporize the media within the flow channel causing a pressurized ejection of a vapor media from the outlet to the tissue to apply thermal energy to the tissue; and
   determining a vapor quality of the vapor media by measuring at least one parameter of the vapor media being ejected during the pressurized ejection of the vapor media to provide a feedback of the vapor quality.

2. The method of claim 1 wherein the media applies energy between 10 and 400,000 Joules to the tissue.

3. The method of claim 1 where introducing the flow of liquid media comprises introducing the flow of liquid media in less than 10 minutes.

4. The method of claim 1 wherein the inductively heating the portion of the probe body comprises applying an electromagnetic energy source to a coil surrounding the flow channel.

5. The method of claim 4 wherein applying the electromagnetic energy source to the coil further comprises heating a wall portion of the flow channel.

6. The method of claim 5 wherein applying the electromagnetic energy source to the coil comprises heating a flow permeable structure in the flow channel.

7. The method of claim 6 wherein the flow permeable structure in the flow channel is selected from the group of woven filaments, braided filaments, knit filaments, metal wool, a microchannel structure, a porous structure, a honeycomb structure and an open cell structure.

8. The method of claim 4 wherein the electromagnetic energy source comprises an energy source selected from the group consisting of a 10 Watt source, 50 Watt source, 100 Watt source, 200 Watt source, 300 Watt source, 400 Watt source and 500 Watt source.

9. The medical system of claim 1, further comprising modulating at least one operating parameter based on the feedback of the vapor quality.

10. A medical system for treating tissue, comprising:
a probe body having a flow channel extending therein to an outlet in a working end;
a coil about at least a portion or the flow channel;
an electromagnetic energy source coupled to the coil, where the electromagnetic energy source induces current in the coil causing energy delivery to a flowable media in the flow channel allowing for pressurized ejection of the heated flowable media directly onto tissue; and
a sensor configured to determine a vapor quality by measuring at least one parameter of the heated flowable media being ejected to provide a feedback of the vapor quality.

11. The medical system of claim 10 further including a source of flowable media coupled to the flow channel.

12. The medical system of claim 10 wherein the electromagnetic energy source is capable of applying energy to the flowable media sufficient to cause a liquid-to-vapor phase change in at least a portion of the flowable media.

13. The medical system of claim 10 wherein the probe carries a sensor selected from the group consisting of a temperature sensor, an impedance sensor, a capacitance sensor and a pressure sensor.

14. The medical system of claim 10 wherein the probe carries a flow channel coupled to an aspiration source.

15. The medical system of claim 10 further comprising a controller capable of modulating at least one operational parameter of the source of flowable media in response to a signal from a sensor.

16. The medical system of claim 15 wherein the controller is capable of modulating a flow of the flowable media.

17. The medical system of claim 15 wherein the controller is capable of modulating a flow of the flowable media to apply between 100 and 400,000 Joules to the tissue.

18. The medical system of claim 15 wherein the flow channel includes a metal portion for contacting the flowable media.

19. The medical system of claim 18 wherein the metal portion comprises a flow permeable structure of the flow channel.

20. The medical system of claim 18 wherein the metal portion comprises at least one filament in the flow channel.

21. The medical system of claim 18 wherein the metal portion comprises a microchannel structure.

22. The medical system of claim 18 wherein the metal portion is selected from the group consisting of woven filaments, braided filaments, knit filaments, metal wool, a porous structure, a honeycomb structure and an open cell structure.

23. The medical system of claim 10 wherein the electromagnetic energy source comprises an energy supply selected from a group consisting of a 10 Watt supply, 50 Watt supply, 100 Watt supply, 200 Watt supply, 300 Watt supply, 400 Watt supply and 500 Watt supply.

24. The medical system of claim 10 wherein the electromagnetic energy source operates in the range of 50 kHz to 2 MHz.

25. The medical system of claim 10, further comprising modulating at least one operating parameter based on the feedback of the vapor quality.

\* \* \* \* \*